(12) United States Patent
Wagner

(10) Patent No.: US 11,130,795 B2
(45) Date of Patent: *Sep. 28, 2021

(54) CD154 PEPTIDES AND METHODS OF INHIBITING CD40 INTERACTIONS WITH CD154

(71) Applicant: The Regents of the University of Colorado, Denver, CO (US)

(72) Inventor: David Wagner, Denver, CO (US)

(73) Assignee: The Regents of the University of Colorado, Denver, CO (US)

( * ) Notice: Subject to any disclaimer, the term of this patent is extended or adjusted under 35 U.S.C. 154(b) by 368 days.

This patent is subject to a terminal disclaimer.

(21) Appl. No.: 15/423,822

(22) Filed: Feb. 3, 2017

(65) Prior Publication Data
US 2017/0355747 A1    Dec. 14, 2017

Related U.S. Application Data

(63) Continuation of application No. 13/880,387, filed as application No. PCT/US2011/056860 on Oct. 19, 2011, now Pat. No. 9,562,088.

(60) Provisional application No. 61/394,699, filed on Oct. 19, 2010.

(51) Int. Cl.
| | | |
|---|---|---|
| *A61K 38/00* | (2006.01) | |
| *C07K 7/00* | (2006.01) | |
| *C07K 14/705* | (2006.01) | |
| *A61K 38/08* | (2019.01) | |
| *A61K 38/10* | (2006.01) | |
| *A61K 38/17* | (2006.01) | |

(52) U.S. Cl.
CPC ........ *C07K 14/70575* (2013.01); *A61K 38/08* (2013.01); *A61K 38/10* (2013.01); *A61K 38/1774* (2013.01)

(58) Field of Classification Search
None
See application file for complete search history.

(56) References Cited

U.S. PATENT DOCUMENTS

| | | |
|---|---|---|
| 6,264,951 B1 | 7/2001 | Armitage et al. |
| 6,319,671 B1 | 11/2001 | U'Ren et al. |
| 6,812,203 B1 | 11/2004 | Pype et al. |
| 7,087,573 B1 | 8/2006 | Lazarus et al. |
| 7,098,322 B2 | 8/2006 | Pype et al. |
| 7,601,335 B2 | 10/2009 | McCutcheon et al. |
| 7,741,280 B2 | 6/2010 | Guichard et al. |
| 8,476,008 B2 | 7/2013 | Nagalla et al. |
| 9,409,987 B2 | 8/2016 | Toporik et al. |
| 9,562,088 B2 | 2/2017 | Wagner |
| 10,882,911 B2 | 1/2021 | Park et al. |
| 2005/0101769 A1 | 5/2005 | Pype et al. |
| 2007/0041971 A1 | 2/2007 | Wagner |
| 2007/0243259 A1 | 10/2007 | Sung et al. |
| 2010/0062471 A1 | 3/2010 | Kantor et al. |
| 2010/0172869 A1 | 7/2010 | Masuoka |
| 2011/0177556 A1 | 7/2011 | Prussak et al. |
| 2011/0229495 A1 | 9/2011 | Wagner |
| 2013/0203719 A1 | 8/2013 | Kalergis et al. |
| 2013/0209463 A1 | 8/2013 | Rotman et al. |
| 2013/0306034 A1 | 11/2013 | Hamedovic et al. |
| 2014/0044641 A1 | 2/2014 | Toporik et al. |
| 2014/0170141 A1 | 6/2014 | Toporik et al. |
| 2016/0296609 A1 | 10/2016 | Oh et al. |
| 2016/0347816 A1 | 12/2016 | Toporik et al. |
| 2016/0356771 A1 | 12/2016 | Smith et al. |
| 2017/0108514 A1 | 4/2017 | Wagner |
| 2017/0232062 A1 | 8/2017 | Rotman et al. |
| 2017/0306034 A1 | 10/2017 | Honczarenko et al. |
| 2017/0355747 A1 | 12/2017 | Wagner |
| 2018/0194829 A1 | 7/2018 | Toporik et al. |
| 2018/0194847 A1 | 7/2018 | Park et al. |
| 2019/0231848 A1 | 8/2019 | Rotman et al. |
| 2019/0263888 A1 | 8/2019 | Wagner, Jr. et al. |
| 2020/0072837 A1 | 3/2020 | Wagner, Jr. et al. |

(Continued)

FOREIGN PATENT DOCUMENTS

| | | |
|---|---|---|
| WO | WO 2007/090280 | 8/2007 |
| WO | WO 2010/055510 | 5/2010 |

(Continued)

OTHER PUBLICATIONS

International Search Report and Written Opinion for International (PCT) Patent Application No. PCT/US2015/022033 dated Jul. 24, 2015, 20 pages.
International Preliminary Report on Patentability for International (PCT) Patent Application No. PCT/US2015/022033 dated Oct. 6, 2016, 17 pages.
Extended European Search Report for European Patent Application No. 15768543.9, dated Mar. 22, 2018, 6 pages.
"Society commits $19.4 Million for New MS Research Projects," National Multiple Sclerosis Society, 2013 retrirved from http://vitaminad.nositio.net/news/New_Research_Fall_2013.pdf, 28 pages.
Anderson et al., "Multiple sclerosis, seizures, and antiepileptics: role of IL-18, IDO, and melatonin," European Journal of Neurology, vol. 18, No. 5, May 2011, pp. 680-685.

(Continued)

*Primary Examiner* — Phillip Gambel
(74) *Attorney, Agent, or Firm* — Foley Hoag LLP; Brendan T. Jones; Wade C. Haaland

(57) ABSTRACT

The present invention provides methods and materials for treating and preventing autoimmune diseases. In particular, the present invention relates to the discovery that small peptides are capable of interacting with CD40, thereby interfering with the ability of CD40 to interact with CD154, which is important in inflammation. The present invention also relate to the use of such peptides in reducing the inflammatory response, and in particular, the autoimmune inflammatory response. The present invention also relates to the use of such short peptides to prevent or reverse autoimmune disease, and particular, diabetes, in individuals suffering from such disease. It also relates to methods and materials for detecting T-cells that express CD40 (Th40 cells). Also provided are kits for reducing inflammation, treating autoimmune diseases, or detecting Th40 cells.

14 Claims, 8 Drawing Sheets

Specification includes a Sequence Listing.

(56) References Cited

U.S. PATENT DOCUMENTS

| | | |
|---|---|---|
| 2020/0297795 A1 | 9/2020 | Wagner, Jr. et al. |
| 2020/0326333 A1 | 10/2020 | Wagner, Jr. et al. |
| 2021/0008162 A1 | 1/2021 | Wagner, Jr. et al. |

FOREIGN PATENT DOCUMENTS

| | | |
|---|---|---|
| WO | WO 2012/154215 | 11/2012 |
| WO | WO-2019/136307 A1 | 7/2019 |
| WO | WO-2020/210726 A1 | 10/2020 |

OTHER PUBLICATIONS

Angelini et al., "Analysis of HLA DP, DQ, and DR alleles in adult Italian rheumatoid arthritis patients," Human Immunology, vol. 34, No. 2, Jun. 1992, pp. 135-141.

Arbour et al., "A new clinically relevant approach to expand myelin specific T cells," Journal of Immunological Methods, vol. 310, No. 1-2, Mar. 2006, pp. 53-61.

Baker et al., "CD40 on NOD CD4 T cells contributes to their activation and pathogenicity," Journal of Autoimmunity, vol. 31, No. 4, Dec. 2008, pp. 385-392.

Benveniste et al., "Molecular regulation of CD40 gene expression in macrophages and microglia," Brain, Behavior, and Immunity, vol. 18, No. 1, Jan. 2004, pp. 7-12.

Bretscher, "The two-signal model of lympocyte activation twenty-one years later," Immunology Today, vol. 13, No. 2, 1992, pp. 74-76.

Fisniku et al., "Disability and T2 MRI lesions: a 20-year follow-up of patients with relapse onset of multiple sclerosis," Brain, vol. 131, No. 3, 2008, pp. 808-817.

Fox, "Clinical features, pathogenesis, and treatment of Sjogren's syndrome," Current Opinion in Rheumatology, vol. 8, No. 5, 1996, pp. 438-445. Abstract Only.

Girvin et al., "CD40/CD40L Interaction is Essential for the Induction of EAE in the Absence of CD28-Mediated Co-stimulation," Journal of Autoimmunity, vol. 18, No. 2, Mar. 2002, pp. 83-94.

Giuliani et al., "Minocycline attenuates T cell and microglia activity to impair cytokine production in T cell-microglia interaction," Journal of Leukocyte Biology, vol. 78, Jul. 135, pp. 135-143.

Goverman et al., "Transgenic mice that express a myelin basic protein-specific T cell receptor develop spontaneous autoimmunity," Cell, vol. 72, No. 4, Feb. 1993, pp. 3018-3027.

Graber et al., "Interleukin-17 in transverse myelitis and multiple sclerosis," Journal of Neuroimmunology, vol. 196, No. 1-2, May 2008, pp. 124-132.

Hafler et al., "Risk alleles for multiple sclerosis identified by a genomewide study," New England Journal of Medicine, vol. 357, No. 9, Aug. 2007, pp. 851-862.

Harrington et al., "Differential tolerance is induced in T cells recognizing distinct epitopes of myelin basic protein," Immunity, vol. 8, No. 5, May 1998, pp. 571-580.

Hemmer et al., "New concepts in the immunopathogenesis of multiple sclerosis," Nature Reviews Neuroscience, vol. 3, No. 4, Apr. 2002, pp. 291-301.

Hoffjan et al., "The genetics of multiple sclerosis: an update 2010," Molecular and Cellular Probes, vol. 24, No. 5, Oct. 2010, pp. 237-243.

Huseby et al., "A pathogenic role for myelin-specific CD8+ T cells in a model for multiple sclerosis," Journal of Experimental Medicine, vol. 194, No. 5, Sep. 2001, pp. 669-679.

Ichikawa et al., "Increased Fas antigen on T cells in multiple sclerosis," Journal of Neuroimmunology, vol. 71, No. 1-2, Dec. 1996, pp. 125-129.

Kent et al., "Expanded T cells from pancreatic lymph nodes of type 1 diabetic subjects recognize an insulin epitope," Nature, vol. 435, No. 7039, May 2005, pp. 224-228.

Liu et al., "CD127 expression inversely correlates with FoxP3 and suppressive function of human CD4+T reg cells," Journal of Experimental Medicine, vol. 203, No. 7, Jul. 2006, pp. 1701-1711.

Lovett-Racke et al., "Decreased dependence of myelin basic protein-reactive T cells on CD28-mediated costimulation in multiple sclerosis patients," Journal of Clincial Investigation, vol. 101, No. 4, Feb. 1998, pp. 725-730.

Lucchinetti et al., "Inflammatory Cortical Demyelination in Early Multiple Sclerosis," New England Journal of Medicine, vol. 365, No. 23, Dec. 2011, pp. 2188-2197.

Lutterotti et al., "Antigen-specific tolerance by autologous myelin peptide-coupled cells: a phase 1 trial in multiple sclerosis," Science Translational Medicine, vol. 5, No. 188, 20 pages.

McMahon et al., "Epitope spreading initiates in the CNS in two mouse models of multiple sclerosis," Nature Medicine, vol. 11, No. 3, 2005, pp. 335-339.

Miller et al., "Antigen presentation in the CNS by myeloid dendritic cells drives progression of relapsing experimental autoimmune encephalomyelitis," Annals of the New York Academy of Sciences, vol. 1103, 2007, pp. 179-191.

Miller et al., "Clinically isolated syndromes," Lancet Neurology, vol. 11, No. 2, Feb. 2012, pp. 157-169.

Miller et al., "The role of magnetic resonance techniques in understanding and managing multiple sclerosis," Brain, vol. 121, Jan. 1998, pp. 3-24.

Miller et al., "Virus-induced autoimmunity: epitope spreading to myelin autoepitopes in Theiler's virus infection of the central nervous system," Advances in Virus Research, vol. 56, 2001, pp. 199-217.

Nyakeriga, et al., "TCR-induced T cell activation leads to simultaneous phosphorylation at Y505 and Y394 of p56(Ick) residues," Cytometry A, vol. 81, No. 9, 2012, pp. 797-805.

O'Connor et al., "Antibodies from inflamed central nervous system tissue recognize myelin oligodendrocyte glycoprotein," Journal of Immunology, vol. 175, No. 3, Aug. 2005, pp. 1974-1982.

Polman et al., "Diagnostic criteria for multiple sclerosis: 2010 revisions to the McDonald criteria," Annals of Neurology, vol. 69, No. 2, Feb. 2011, pp. 292-302.

Polman et al., "Drug treatment of multiple sclerosis," Medicine Cabinent, vol. 173, Dec. 2000, pp. 398-402.

Polman et al., "Multiple sclerosis diagnostic criteria: three years later," Multiple Sclerosis Journal, vol. 11, No. 1, Feb. 2005, pp. 5-12.

Rivera et al., "Using Th40:Treg Ratio as a Predictor of Multiple Sclerosis and Other Autoimmune Diseases," University of Notre Dame, 2013, retrieved from http://www.ucdenver.edu/academics/colleges/medicalschool/centers/WebbWaring/Documents/Summer%20Students%/202013/Erika%20Rivera%20Poster%20Final.pdf, 1 page.

Sawcer et al., "Genetic risk and a primary role for cell-mediated immune mechanisms in multiple sclerosis," Nature, vol. 476, No. 7359, pp. 214-219.

Sawcer, "The complex genetics of multiple sclerosis: pitfalls and prospects," Brain, vol. 131, Dec. 2008, pp. 3118-3131.

Siebert et al., "An analytical workflow for investigating cytokine profiles," Cytometry A, vol. 73, No. 4, Apr. 2008, pp. 289-298.

Smith et al., "Multi-peptide coupled-cell tolerance ameliorates ongoing relapsing EAE associated with multiple pathogenic autoreactivities," Journal of Autoimmunity, vol. 27, No. 4, Jan. 2007, pp. 218-231.

Steck et al., "Genetics of type 1 diabetes," Clinical Chemistry, vol. 57, No. 2, Feb. 2011, pp. 176-185.

Thorsby et al., "Particular HLA-DQ molecules play a dominant role in determining susceptibility or resistance to Type 1 (insulin-dependent) diabetes mellitus," Diabetologia, vol. 36, No. 5, May 1993, pp. 371-377.

Vaitaitis et al., "CD40 interacts directly with RAG1 and RAG2 in autoaggressive T cells and Fas prevents CD40 induced RAG expression," Cellular and Molecular Immunology, vol. 10, No. 6, Nov. 2013, pp. 483-489.

Vaitaitis et al., "The Expanding Role of TNF-Receptor Super Family Member CD40 (tnfrsf5) in Autoimmune Disease: Focus on Th40 Cells," Current Immunology Reviews, vol. 6, No. 2, 2010, pp. 130-136. Abstract Only.

(56) References Cited

OTHER PUBLICATIONS

Waid et al., "A unique T cell subset, Th40, are pathogenic and diagnostic in mulitple sclerosis," Journal of Immunology, vol. 186, No. 1, Apr. 2011, Meeting Abstract.
Wucherpfennig et al., "A Review of T-Cell Receptors in Multiple Sclerosis: Clonal Expansion and Persistence of Human T-Cells Specific for an immunodominant Myelin Basic Protein Peptidea," Annals of the New York Academy of Sciences, vol. 756, No. 1, Jul. 1995, pp. 241-258.
Zhang et al., "T cell and antibody responses in remitting-relapsing experimental autoimmune encephalomyelitis in (C57BL/6 x SJL) F1 mice," Journal of Neuroimmunology, vol. 148, No. 1-2, Mar, 2004, pp. 1-10.
Official Action for European Application No. 11 835 055.2, dated Jun. 14, 2016, 4 pages.
Official Action for European Application No. 11 835 055.2, dated Feb. 9, 2017, 4 pages.
Aarts, Suzanne A.B. et eh, "Inhibition of CD4-TRAF6 interactions by the small molecule inhibitor 6877002 reduces neuroinflammation," Journal of Neuroinflammation, 2017, vol. 14, Iss. 105, pp. 105-118.
Armitage, Richard J. et al., "CD40L: a multi-functional ligand," Seminars in Immunology, 1993, vol. 5, pp. 401-412.
Balasa, Balaji, et al., "CD40 Ligand-CD40 Interactions Are Necessary for the Initiation of Insulitis and Diabetes in Nonobese Diabetic Mice," The Journal of Immunology, 1997, vol. 159, pp. 4620-4627.
Becker, Thalia, et el., "CD40, an extracellular receptor for binding and uptake of Hsp70-peptide complexes," The Journal of Cell Biology, 2002, vol. 158, No. 7, pp. 1277-1285.
Bourgeois, Christine, et al., "A Role for CD40 Expression on CD8+ T cells in the Generation of CD8+ T Cell Memory," Science, 2002, vol. 297, pp. 2060-2063.
Carter, Jessica, et al., "CD40 engagement of CD4+CD40+ T cells in a neo-self antigen disease model ablates CTLA-4 expression and indirectly impacts tolerance," European Journal of Immunology, 2012, vol. 42, pp. 424-435.
Chatzigeorgiou, Antonios, et al., "Blocking CD4O-TRAF6 signaling is a therapeutic target in obesity-associated insulin resistance," PNAS, 2014, vol. 111, No. 7, pp. 2686-2691.
Cipollone, F., et al., "Enhanced soluble CD4O ligand contributes to endothelial cell dysfunction in vitro and rnonocyte activation in patients with diabetes mellitus: effect of improved metabolic control," Diabetologia, 2005, vol. 48, pp. 1216-1224.
Cooper, Cristine J., et al., "Cutting Edge: TCR Revision Occurs in Germinal Centers," The Journal of Immunology, 2004, vol. 173, pp. 6532-6536.
Davidson, Anne, et al. "Co-Stimulatory Blockade in the Treatment of Murine Systemic Lupus Erythematosus," Ann. N.Y. Acad. Sci., 2003, vol. 987, pp. 188-198.
De Ramon, Laura, et al. "CD154-CD40 T-cell co-stimulation pathway is a key mechanism in kidney ischemia-reperfusion injury," Kidney International, 2015, vol. 88, pp. 538-549.
Devaraj, Sridevi, et al., "Increased Monocytic Activity and Biornarkers of Inflammation in Patients With Type 1 Diabetes," Diabetes, 2006, vol. 55, pp. 774-779.
Durie, Fiona H., et al., "Prevention of Collagen-Induced Arthritis with an Antibody to gp39, the Ligand for CD40," Science, 1993, vol. 261, pp. 1328-1330.
Ellmark, Peter, et al., "Modulation of the CD40-CD40 ligand interaction using human anti-CD40 single-chain antibody fragments obtained from the n-CoDeR phage display library," Immunology, 2002, vol. 106, pp. 456-463.
Fanslow, William C., et al., "Recombinant CD40 Ligand Exerts Potent Biologic Effect on T Cells," Journal of Immunology, 1994, vol. 152, pp. 4262-4269.
Goodnow, Christopher C., "Pathways for self-tolerance and the treatment of autoimmune diseases," Lancet, 2001, vol. 357, pp. 2115-2121.

Grabstein, Kenneth H., "The Regulation of T Cell-Dependent Antibody Formation in Vitro by CD40 Ligand and IL-2," The Journal of Immunology, 1993, vol. 150, No. 8, pp. 3141-3147.
Grossman, Michael E. "Avoiding Tolerance Against Prostatic Antigens With Subdominant Peptide Epitopes," Journal of Immunotherapy, 2001, vol. 23, Issue 3, pp. 237-241.
Guo, Yanxia, et al., "CD40L-Dependant Pathway is Active at Various Stages of Rheumatoid Arthritis Disease Progression," The Journal of Immunology, 2017, vol. 198, pp. 4490-4501.
Haixiang, et al., "Targeting CD40 with a Selective Phage Display Derived Peptide," pp. 61-74.
Hernandez, Maria Genevive H., et al., "CD40-CD40 Ligand Interaction between Dendritic Cells and CD8+ T Cells Is Needed to Stimulate Maximal T Cell Responses in the Absence of CD4+ T Cell Help," The Journal of Immunology, 2007, vol. 178, pp. 2844-2852.
Homann, Dirk, et al., "CD40L Blockade Prevents Autoimmune Diabetes by Induction of Bitypic NK/DC Regulatory Cells," Immunity, 2002, vol. 16, pp. 403-415.
Howard, Laurence M., et al., "Immunotherapy Targeting the CD40/CD154 Costimulatory Pathway for Treatment of Autoimmune Disease," Autoimmunty, 2004, vol. 37, Issue 5, pp. 411-418.
Khan, Srijit, et al., "Differential peptide binding to CD40 evokes counteractive responses," Human Immunology, 2012, vol. 73, pp. 465-469.
Kitagawa, Minetake, et al., "Identification of three novel peptides that inhibit CD40-CD154 interaction," Mod. Rheumatol., 2005, vol. 15, pp. 423-426.
Kobata, Tetsuji, et al., "Role of costimulatory molecules in autoimmunity," Reviews in Immunogenetics, 2000, vol. 2, pp. 74-80.
Lederman, Seth, et al., "Molecular Interactions Mediating T-B Lymphocyte Collaboration in Human Lymphoid Follicles: Roles of T Cell-B Cell-Activating Molecule (5c8 Antigen) and CD40 in Contact-Dependent Help," The Journal of Immunology, 1992, vol. 149, No. 12, pp. 3817-3826.
Lederman, Seth, et al., "Identification of a Novel Surface Protein on Activated CD4+ T Cells That Induces Contact-dependant B Cell Differentiation (Help)," J. Exp. Med., 1992. vol. 175, pp. 1091-1101.
Marsh, Steven G.E., "Nomenclature for factors of the HLA system, updated Jan. 2012," Human Immunology, 2012, vol. 73, pp. 593-596.
McWhirter, Sarah M., et al., "Crystallographic analysis of CD40 recognition and signaling by human TRAF2," Proc. Natl. Acad. Sci. USA, 1999, vol. 96, pp. 8408-8413.
Munroe, Melissa E., et al., "Pro-Inflammatory Adaptive Cytokines and Shed Tumor Necrosis Factor Receptors are Elevated Preceding Systemic Lupus Erythematosus Disease Flare," Arthritis Rheumatol., 2014, vol. 66, Issue 7, pp. 1888-1899.
Pullen, Steven S., et al., "CD40 Signaling through Tumor Necrosis Factor Receptor-associated Factors (TRAFs)," The Journal of Biological Chemistry, 1999, vol. 274, No. 20, pp. 14246-14254.
Ramsdell, Fred, et al., "CD40 Ligand Acts as a Costimulatory Signal for Neonatal Thymic Gamma Delta T Cells," The Journal of Immunology, 1994, vol. 152, pp. 2190-2197.
Resetkova, Erika, et al.. "Antibody to gp39, the Ligand for CD40 Significantly Inhibits the Humoral Response from Graves' Thyroid Tissues Xenografted into Severe Combined Immunodeficient (SCID) Mice," Thyroid, 1996, vol. 6, No. 4, pp. 267-273.
Richards, Julie L., et al., "A peptide containing a novel FPGN CD40-binding sequence enhances adenoviral infection of murine and human dendritic cells," Eur. J. Biochem., 2003, vol. 270, pp. 2287-2294.
Russo, Simona, et al., "Platelet-Activating Factor Mediates CD40-Dependent Angiogenesis and Endothelial-Smooth Muscle Cell Interaction," The Journal of Immunology, 2003, pp. 5489-5497.
Sarawar, Sally R., et al., "Stimulation via CD40 can substitute for CD4 T cell function in preventing reactivation of latent herpesvirus," PNAS, 2001, vol. 98, pp. 6325-6329.
Schonbeck, U., et al., "The CD40/CD154 receptor/ligand dyad," CMLS—Cellular and Molecular Life Sciences, 2001, vol. 58, pp. 4-43.

(56) References Cited

OTHER PUBLICATIONS

Schonbeck, Uwe, et al., "Molecules in focus, CD154 (CD40 ligand)," The International Journal of Biochemistry & Cell Biology, 2000, vol. 32, pp. 687-693.
Seko, Yoshinori, et al., "Expression of Tumor Necrosis Factor (TNF) Receptor/Ligand Superfamily Co-Stimulatory Molecules CD40, CD30L, CD27L, and Ox40L in Murine Hearts with Chronic Ongoing Myocarditis Caused by Coxsackie Virus B3," J. Pathol., 1999, vol. 188, pp. 423-430.
Stumpf, Christian, et al., "Enhanced levels of CD154 (CD40 ligand) on platelets in patients with chronic heart failure," The European Journal of Heart Failure, 2003, vol. 5, pp. 629-637.
Sun, Yonglian, et al., "Co-stimulation agonists as a new immunotherapy for autoimmune diseases," TRENDS in Molecular Medicine, 2003, vol. 9, No. 11, pp. 483-489.
Toubi, Elias, et al., "The Role of CD40-CD154 Interactions in Autoimmunity and the Benefit of Disrupting this Pathway," Autoimmunity, 2004, vol. 37, pp. 457-464.
Townsend, Kirk P., et al., "CD40 signaling regulates innate and adaptive activation of microglia in response to amyloid b-peptide," Eur. J. Immunol., 2005, vol. 35, pp. 901-910.
Vaitaitis, Gisela M., et al., "Cutting Edge: CD40-Induced Expression of Recombination Activating Gene (RAG) 1 and RAG2: A Mechanism for the Generation of Autoaooressive T Cells in the Periphery," The Journal of Immunology, 2003, vol. 170, pp. 3455-3459.
Vaitaitis, Gisela M., et al., "High Distribution of CD40 and TRAF2 in Th40 T Cell Rafts Leads to Preferential Survival of this Auto-Aggressive Population in Autoimmunity," PLoS ONE, 2008, vol. 3, Issue 4, pp. e2076:1-11.
Vaitaitis, Gisela M., et al., "CD40 glycoforms and TNF-receptors 1 and 2 in the formation of CD40 receptor(s) in autoimmunity," Molecular Immunology, 2010, vol. 47, pp. 2303-2313.
Vaitaitis, Gisela M., et al., "Galectin-9 Controls CD40 Signaling through a Tim-3 Independent Mechanism and Redirects the Cytokine Profile of Pathogenic T Cells in Autoimmunity," PLoS ONE, 2012, vol. 7, Issue, 6, pp. 38708:1-13.
Vaitaitis, Gisela M., et al "An Alternative Role for Foxp3 as an Effector T Cell Regulator Controlled through CD40," The Journal of Immunology, 2013, vol. 191, pp. 717-725.
Vaitaitis, Gisela M., et al., "Th40 cells (CD4+CD40+ Tcells) drive a more severe form of Experimental Autoimmune Encephalomyelitis than conventional CD4 T cells." PLoS ONE, 2017, vol. 12, pp. e0172037.
Varo, Nerea, et al., "Soluble CD40L—Risk Prediction After Acute Coronary Syndromes," Circulation, 2003, vol. 108, pp. 1049-1052.
Wagner Jr., David H., et al "Increased expression of CD40 on thymocytes and peripheral T cells in autoimmunity: A mechanism for acquiring changes in the peripheral T cell receptor repertoire," International Journal of Molecular Medicine, 1999, vol. 4, pp. 231-242.
Wagner Jr., David H., et al., "Expression of CD40 identifies a unique pathogenic T cell population in type 1 diabetes," PNSA, 2002, vol. 99, No. 6, pp. 3782-378.
Waid, D,M., et al,, "Peripheral CD4loCD40+ auto-aggressive T cell expansion during insulin-dependent diabetes mellitus," Eur. J. Immunol., 2004, vol. 34, pp. 1488-1497.
Waid, D.M., et al., "A unique T cell subset described as CD4loCD40+ T cells (TCD40) in human type 1 diabetes," Clinical Immunology, 2007, vol. 124, pp. 138-148.
Waid, D.M., et al., "Disruption of the homeostatic balance between autoaggressive (CD4+CD40+) and regulatory (CD4+CD25+ FoxP3+) T cells promotes diabetes," Journal of Leukocyte Biology, 2008, vol. 64, pp. 431-439.
Waid, D.M., et al., "Defining a New Biomarker for the Autoimmune Component of Multiple Sclerosis: Th40 cells," J. Neuroimmunol 2014, vol. 270, pp. 75-85.
Notice of Allowance for European Application No. 11 835 055.2, dated Dec. 11, 2017, 5 pages.
International Search Report and Written Opinion for International (PCT) Patent Application No. PCT/US11/56860 dated May 4, 2012, 11 pages.
International Preliminary Report on Patentability for International (PCT) Patent Application No. PCT/US11/56860 dated May 2, 2013, 8 pages.
Official Action for European Application No. 11 835 055.2, dated Nov. 20, 2014, 5 pages.
Attwood, "The Babel of Bioinformatics," Science, 2000, vol. 290(5491), pp. 471-473, 5 pages.
Karpusas et al., "2 Å crystal structure of an extracellular fragment of human CD40 ligand," Structure, 1995, vol. 3(10), pp. 1031-1039.
Skolnick et al., "From genes to protein structure and function: novel applications of computational approaches in the genomic era," Trends in Biotech., 2000, vol. 18(1), pp. 34-39.
Vaitaitis et al., "A CD40-targeted peptide controls and reverses type 1 diabetes in NOD mice," Diabetologia, 2014, vol. 57, pp. 2366-2373.
Official Action for U.S. Appl. No. 13/880,387, dated Jun. 24, 2015, 15 pages.
Final Action for U.S. Appl. No. 13/880,387, dated Feb. 18, 2016, 8 pages.
Advisory Action for U.S. Appl. No. 13/880,387, dated May 27, 2016, 4 pages.
Notice of Allowance for U.S. Appl. No. 13/880,387, dated Sep. 21, 2016, 9 pages.
Aarts et al., "The CD40-CD40L dyad in Experimental Autoimmune Encephalomyelitis and Multiple Sclerosis," Chapter 2 Front. Immunol., 8(1791): 24-45 (2017).
Abdelhak et al., "Primary Progressive Multiple Sclerosis: Putting Together the Puzzle," Frontiers in Neurology, 8:234 (2017).
Alaoui-Lsmaili et al., "Design of second generation therapeutic recombinant bone morphogenetic proteins," Cytokine & Growth Factor Reviews, 20: 501 -507 (2009).
Barker et al., "Prediction of Autoantibody Positivity and Progression to Type 1 Diabetes: Diabetes Autoimmunity Study in the Young (DAISY)," Journal of Clinical Endocrinology & Metabolism, 89(8):3896-3902 (2004).
Bonifacio, "Predicting Type 1 Diabetes Using Biomarkers," Diabetes Care, 38: 989-996 (2015).
Boon et al., "Prevention of Experimental Autoimmune Encephalomyelitis in the Common Marmoset (Allithrix jacchus) Using a Chimeric Antagonist Monoclonal Antibody Against Human CD40 Is Associated with Altered B Cell Response," J. Immunol., 167: 2942-2949 (2001).
Bowie et al., "Deciphering the Message in Protein Sequences: Tolerance to Amino Acid Substitutions," Science, 247(4948): 1306-1310 (1990).
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, 111:2129-2138(1990).
Christensen et al., "Systemic Inflammation in Progressive Multiple Sclerosis Involves Follicular T-Helper, Th17- and Activated B-Cells and Correlates with Progression," Plos One, 8(3): e57820 (2013).
Extended European Search Report for EP Application No. PCT/US2015/022033 dated Mar. 22, 2018.
Garlichs et al., "Upregulation of CD40 and CD40 ligand (CD154) in patients with moderate hypercholesterolemia," Circulation, 104: 2395-2400 (2001).
Gerritse et al., "CD40-CD40 ligand interactions in experimental allergic encephalomyelitis and multiple sclerosis," PNAS, 93: 2499-2504 (1996).
Guo et al., "Protein tolerance to random amino acid change," PNAS, 101(25): 9205-9210 (2004).
Lezzi et al., "CD40-CD40L cross-talk integrates strong antigenic signals and microbial stimuli to induce development of IL-17-producing CD4+ T cells," Proc Natl Acad Sci USA, 106: 876-881 (2009).
Llonen et al., "Abnormalities within CD4 and CD8 T lymphocyte subsets in type 1 (insulin-dependent) diabetes," Clin, exp. Immunol., 85(2): 278-281 (1991).

(56) References Cited

OTHER PUBLICATIONS

International Preliminary Report on Patentability for International Application No. PCT/US2015/022033 dated Jul. 24, 2015.
International Search Report and Written Opinion for International Application No. PCT/US2019/012425 dated May 7, 2019.
International Search Report and Written Opinion for International Application No. PCT/US2020/027804 dated Jun. 22, 2020.
Jensen et al., "Increased T cell expression of CD154 (CD40-ligand) in multiple sclerosis," European Journal of Neurology, 8:321-328 (2001).
King et al., "The Use of Animal Models in Diabetes Research," British Journal of Pharmacology, 166: 877-894 (2012).
Kuo et al., "IL-17 and CD40 ligand synergistically stimulate the chronicity of diabetic nephropathy," Nephrol Dial Transplant, 33: 248-256 (2018).
Laman et al., "Protection of marmoset monkeys against EAE by treatment with a murine antibody blocking CD40 (mu5D12)," Eur. J. Immunol., 32: 2218-2228 (2002).
Laman et al., "Therapy with antibodies against CD40L (CD154) and CD44-variant isoforms reduces experimental autoimmune encephalomyelitis induced by a proteolipid protein peptide," Multiple Sclerosis, 4:147-153 (1998).
Mackey et al., "Calcifications, arterial stiffness, and atherosclerosis," Atherosclerosis, Large Arteries and Cardiovascular Risk. Adv Cardiol., 44: 234-244 (2008).
Mayo Clinic Diabetes, mayoclinic.org/diseases-conditions/diabetes/symptoms-causes/syc-2037 1444?; pp. 1-7; mayoclinic.org/diseases-conditions/diabetes/diagnosis-treatment/drc-20371451 ?p=1; pp. 1-1 1, downloaded Feb. 20, 2012. (Year: 2012).
Notice of Allowance and Fees Due for U.S. Appl. No. 13/880,387 dated Sep. 21, 2016.
Pawson et al., "Assembly of Cell Regulatory Systems Through Protein Interaction Domains," Science, 300: 445-452 (2003).
Seijkens et al., "CD40-CD40L: linking pancreatic, adipose tissue and vascular inflammation in type 2 diabetes and its complications," Diab Vase Dis Res, 10:115-122 (2012).
Vaitaitis et al., "CD40-mediated signalling influences trafficking, T-cell receptor expression, and T-cell pathogenesis, in the NOD model of type 1 diabetes," Immunology, 152: 243-254 (2017).
Winer et al., "B Lymphocytes promote insulin resistance through modulation of T Lymphocytes and production of pathogenic IgG antibody," Nat Med, 17: 610-617 (2011).

CD154 PEPTIDES AND METHODS OF INHIBITING CD40 INTERACTIONS WITH CD154

This application contains a Sequence Listing submitted via electronic text file entitled OPB-00101 SL.txt having a size in bytes of 10,695 bytes and created Nov. 2, 2020. The information contained in the electronic file is hereby incorporated by reference in its entirety pursuant to 37 CFR § 1.52(e)(5).

FIELD OF THE INVENTION

The present invention relates to peptides that inhibit the interaction of CD40 and CD154, and the use of such compounds in modulating T-cell activity and in treating disease.

BACKGROUND

Inflammation normally occurs in response to infection by invading micro-organisms. This inflammatory response is beneficial because it is an important part in localizing the infecting agent for removal by the immune system. However, in autoimmunity there is no infection, yet severe inflammation is present. The inflammation in this case, referred to as aseptic chronic inflammation, is detrimental since it destroys normal tissues. The results of this aseptic inflammation are life-altering and in some cases life-threatening. Moreover, as with acute inflammation, this process is mediated by immune cells, including T-cells.

A major concern for modern medicine is how to control aseptic, chronic inflammation (ACI) such as that which occurs during autoimmune diseases, as well as how to control acute inflammation resulting from trauma. Inflammation, both chronic and acute, leads to tissue degeneration and eventual loss of function of major organs. ACI is not limited to a single disease, but is instrumental in numerous autoimmune diseases including, but not limited to type 1 diabetes, multiple sclerosis, systemic lupus erythematosa, rheumatoid arthritis, Crohn's disease, inflammatory bowel disease, chronic obstructive pulmonary disease including types of autoimmune asthma, atherosclerosis, vasculitis, hypertension, thyroiditis including Hashimoto's and Graves diseases, primary biliary cirrhosis, Paget's disease, Addison's disease, acute respiratory distress syndrome, acute lung injury, and ACI associated with organ transplantation.

Autoimmune disorders are classified into two types: organ-specific (directed mainly at one organ) and non-organ-specific (widely spread throughout the body). Examples of organ-specific autoimmune disorders are insulin-dependent Type 1 diabetes which affects the pancreas; Hashimoto's thyroiditis and Graves' disease, which affect the thyroid gland; pernicious anemia, which affects the blood; Addison's disease, which affects the adrenal glands; chronic active hepatitis, which affects the liver; myasthenia gravis which affects the muscle; and multiple sclerosis, which affects tissue of the nervous system. An example of a non-organ-specific autoimmune disorders is rheumatoid arthritis. Autoimmune diseases are often chronic, debilitating, and life-threatening. The National Institutes of Health (NIH) estimates that up to 23.5 million Americans suffer from autoimmune disease and that the prevalence is rising. It has been estimated that autoimmune diseases are among the ten leading causes of death among women in all age groups up to 65 years.

Acute inflammation, as observed during trauma or sepsis, is also immune cell mediated. While all of the molecular mediators in this process have not yet been identified, a prominent role for T cells, macrophages/monocytes, neutrophils etc., is strongly implicated. Therefore, a means to modulate these cell types would necessarily control the inflammatory response.

A unique T-cell subset has been shown to be instrumental in the development of autoimmune disease. These cells are phenotypically characterized as CD4loCD40+ (Waid, D. M., et al. (2004.) Euro. J. of Immunol. 34:1488; Vaitaitis, G. M., et al. (2003). Cutting Edge, J. Immunol. 170:3455; Wagner, D. H., Jr., et al. (2002). Proc. Natl. Acad. Sci. U.S.A. 99:3782; Wagner, D. H., Jr., et al. (1999). Intl. J. of Mole. Med. 4:231) and are referred to as Th40 cells. CD40 expression typically is associated with antigen presenting cells and the majority of prior art describes CD40 as being expressed on B cells, macrophages, monocytes etc. However, CD40 proteins are also expressed on T-cells (Waid, D. M., et al. (2004). Eur. J. of Immunol. 34:1488; Vaitaitis, G. M., et al. (2003). Cutting Edge, J. Immunol. 170:3455; Wagner, D. H., Jr., et al. (2002). Proc. Natl. Acad. Sci. U.S.A. 99:3782; Wagner, D. H., Jr., et al. (1999). Intl. J. of Mole. Med. 4:231; Bourgeois, C., et al. (2002). Science. 297:2060; Fanslow, W. C., et al. (1994). J. of Immunol. 152:4262; Ramsdell, F., et al. (1994). J. of Immunol. 152:2190; Grabstein, K. H., et al. (1993). J. of Immunol. 150:3141; Armitage, R. J., et al. (1993). Sem. in Immunol. 5:401; Cooper, C. J., et al. (2004). J. Immunol. 173:6532). While Th40 cells comprise a proportion of the peripheral CD4+ compartment in naïve, non-autoimmune mice (Waid, D. M., et al. (2004). Eur. J. of Immun. 34:1488; Wagner, D. H., Jr., et al. (1999). Intl. J. of Mole. Med. 4:231), and in humans (Waid. D. M, et al. (2007). Clin. Immunol. 124:138), this proportion is drastically expanded to as much as 50% of the CD4+ compartment in autoimmune prone mice (Waid, D. M., et al. (2004). Eur. J. of Immunol. 34:1488; Wagner, D. H., Jr., et al. (2002). Proc. Natl. Acad. Sci. U.S.A. 99:3782; Wagner, D. H., Jr., et al. (1999). Intl. J. of Mole. Med. 4:231) and humans (Waid. D. M., et al. (2007). Clin. Immunol. 124:138). These T-cells do not express early activation markers and occur in the naïve phenotype of non-challenged mice. In diabetic NOD mice, Th40 cells occur at exaggerated levels in spleen, lymph nodes and the pancreas, even prior to diabetes onset (Waid, D. M., et al. (2004). Eur. J. of Immunol. 34:1488; Wagner, D. H., Jr., et al. (2002). Proc. Natl. Acad. Sci. U.S.A. 99:3782). An elevated number and percentage of these T-cells is seen in peripheral blood of type 1 diabetic patients when compared to non-autoimmune controls and type 2 diabetic patients (Waid. D. M., et al. (2007). Clin. Immunol. 124:138).

The observed increase in Th40 cells could mean that those T-cells are antigen responsive or that CD40 expression is activation induced. Furthermore, several diabetogenic T cell clones are CD40+ (Wagner, D. H., Jr., et al. (2002). Proc. Natl. Acad. Sci. U.S.A. 99:3782). Purified primary Th40 cells from diabetic NOD mice and from pre-diabetic NOD (12-weeks of age) mice successfully transfer type 1 diabetes to NOD.scid recipients, directly demonstrating pathogenicity of that T cell subset (Waid, D. M., et al. (2004). Eur. J. of Immunol. 34:1488; Wagner, D. H., Jr., et al. (2002). Proc. Natl. Acad. Sci. U.S.A. 99:3782). It has been shown that Th40 cells infiltrate islet beta cells destroying insulin production thus suggesting islet antigen specificity (Waid, D. M., et al. (2004). Eur. J. of Immunol. 34:1488; Wagner, D. H., Jr., et al. (2002). Proc. Natl. Acad. Sci. U.S.A. 99:3782). It has also been shown that Th40 cells are required for diabetes transfer. Peripheral (spleen and regional lymph node) T-cells that were CD40 depleted, then CD25, Treg, depleted were not capable of transferring diabetes to Scid recipients. Even though Tregs were removed, if the autoaggressive CD40+ T cells subset is absent, disease transfer does not occur.

While Th40 cells are important in the development of autoimmunity, another important factor is expression of the CD40-Ligand, CD154. CD154 is temporally induced on activated T cells in response to CD3/TCR stimulation (Lederman, S., et al. (1992). J. of Exp. Med. 175:1091). CD154 expression has also been demonstrated to be present on platelets, monocytes, basophils, eosinophils, dendritic cells, fibroblasts, smooth muscle, and endothelial cells (Russo, S., et al. (2003). J. Immunol. 171:5489; Stumpf, C., et al. (2003). Eur. J. Heart Fail. 5:629; Schonbeck, U., et al. (2001). Cell Mol. Life Sci. 58:4). CD154 is a member of the tumor necrosis factor (TNF) super-family and a soluble form of CD154 (sCD154) has been described (Russo, S., et al. (2003). J. Immunol. 171:5489; Stumpf, C., et al. (2003). Eur. J. Heart Fail. 5:629; Toubi, E., et al. (2004). Autoimmunity 37:457). Therefore, sCD154 may act like a cytokine (Stumpf, C., et al. (2003). Eur. J. Heart Fail. 5:629). Even though CD153 has not been genetically linked in T1D studies, sCD154 is significantly elevated in T1D and may play a role in the disease process (Varo, N., et al. (2003). Circulation 107:2664; Cipollone, F., et al. (2005). Diabetologia 48:1216; Devaraj, S., et al. (2006). Diabetes 55:774). The importance of CD40-CD154 interaction in autoimmunity has been established (Wagner, D. H., Jr., et al. (2002). Proc. Natl. Acad. Sci. U.S.A. 99:3782; Kobata, T., et al. (2000). Rev. Immunogenet. 2:74; Homann, D., et al. (2002). Immunity. 16:403; Goodnow, C. C. (2001). Lancet 357: 2115; Balasa, B., et al. (1997). J. of Immunol. 159:4620). Blocking CD40-CD154 interaction prevents collagen induced arthritis (Durie, F. H., et al. (1993). Science. 281: 1328), experimental autoimmune encephalitis (Howard, L. M., et al. (2004). Autoimmunity. 37:411), prostatitis (Grossman, M. E., et al. (2001). J. Immunother. 24:237), and importantly type 1 diabetes in the NOD mouse model (Balasa, B., et al. (1997). J. of Immunol. 159:4620). In the diabetes model it was essential to administer a CD154 blocking antibody to NOD mice at 3-weeks of age; at 9-weeks, blocking antibodies had no effect on diabetes prevention (Balasa, B., et al. (1997). J. of Immunol. 159: 4620).

Previous work has also demonstrated that the Th40 cell subset induces RAG1 and RAG2 transcription, translation and nuclear translocation (Vaitaitis, G. M., et al. (2003). Cutting Edge, J. Immunol. 170:3455) when CD40 is engaged. CD3 engagement does not induce RAG1 or RAG2 in T cells (Vaitaitis, G. M., et al. (2003). Cutting Edge, J. Immunol. 170:3455). Subsequent to RAG1/RAG2 induction, CD40-mediated TCR revision occurs in peripheral T cells (Vaitaitis, G. M., et al. (2003). Cutting Edge, J. Immunol. 170:3455). CD40 induction of TCR revision is RAG dependent. T cells isolated from a TCR-Tg mouse undergo TCR revision when CD40 engaged, but T cells from the TCR-Tg.RAG-/- mouse do not TCR revise when CD40 engaged (Wagner, D. H., Jr., et al. (1999). Intl. J. of Mole. Med. 4:231).

Multiple treatment options have been put forward to address and control both chronic and acute inflammation. Many approaches use non-steroidal anti-inflammatory drugs (NSAIDS) that attack the production of leukotrienes and prostaglandins, cellular products that cause localized inflammation. Other approaches use more powerful immunosuppressant drugs such as cyclophosphamide, methotrexate and azathioprine that suppress the immune response and stop the progression of the disease. Still other treatments involve the use of monoclonal antibodies designed to alter the immune responses to self-tissues, as occurs during autoimmune diseases. However, all of these treatments often have severe, long-term side effects.

Thus, there exists a need in the art for safer and more effective methods for treatment and prevention of autoimmune diseases. The present invention addresses this need by describing a novel method for treatment of autoimmune diseases.

SUMMARY OF THE INVENTION

The present developments provide a novel method for modulating inflammation, and, inflammation that arises as a result of an autoimmune disease. The developments are based on the knowledge that interaction of CD40-ligand (CD154 protein) with CD40 protein expressed on T-cells (Th40 cells), is important in the development of autoimmune disease. The developments are also based on the elucidation of the critical residues in CD40 and CD154 that are important for this interaction. The present developments relate to blocking the interaction between a CD40 protein and a CD154 protein through the use of small peptides that interact with the CD40 protein at a site where the CD154 protein would normally bind. The present developments also relate to using such peptides to reduce the level of Th40 cells, thereby reducing the severity of disease. Finally, the present developments also relate to novel methods for detecting Th40 cells.

One embodiment of the present developments is a peptide that interacts with a CD40 protein in such a manner as to modulate inflammation. Preferred peptides are those that are less than 25 amino acids in length, and that bind to a CD40 protein, thereby inhibiting its interaction with a CD154 protein. Preferred peptides are those that comprise a portion of the CD40 binding site from a CD154 protein.

One embodiment of the present developments is a method to inhibit the interaction between a CD40 protein and a CD154 protein, the method comprising contacting the CD40 protein with a peptide that interacts with the CD40 protein. Preferred peptides interact with the CD40 protein at the CD154-binding site. Preferably such peptides are less than 20 amino acids in length. Even more preferred peptides are those consisting of an amino acid sequence selected from the group consisting of SEQ ID NOs 3-10.

One embodiment of the present developments is a method to modulate inflammation in an animal or a culture of cells, the method comprising administering to said animal, or said cells, a peptide that interacts with a CD40 protein in such a manner as to modulate inflammation. Preferred peptides are those that interact with the CD40 protein at the CD154-binding site, thereby modulating inflammation. Preferred peptides modulate inflammation by reducing the level of Th40 cells to no more than 25% of the total T-cell population. Such methods can be used to treat autoimmune diseases such as diabetes.

Another embodiment of the present developments is a means to detect autoagressive T-cells, the method comprising contacting a population of T-cells with a peptide that binds the CD40 protein and detecting the CD-40 bound peptide.

One embodiment of the present developments is a method to identify a patient at risk for developing an autoimmune disease, the method comprising obtaining a sample containing T-cells from a patient to be tested, contacting the sample with a peptide that binds the CD40 protein, detecting the CD-40 bound peptide, and determining the level of Th40 cells from the amount of CD40 bound, wherein a level of Th40 cells greater than 25% of the total T-cell population indicates the patient is at risk for developing an autoimmune disease.

DETAILED DESCRIPTION OF THE INVENTION

Figure 1:
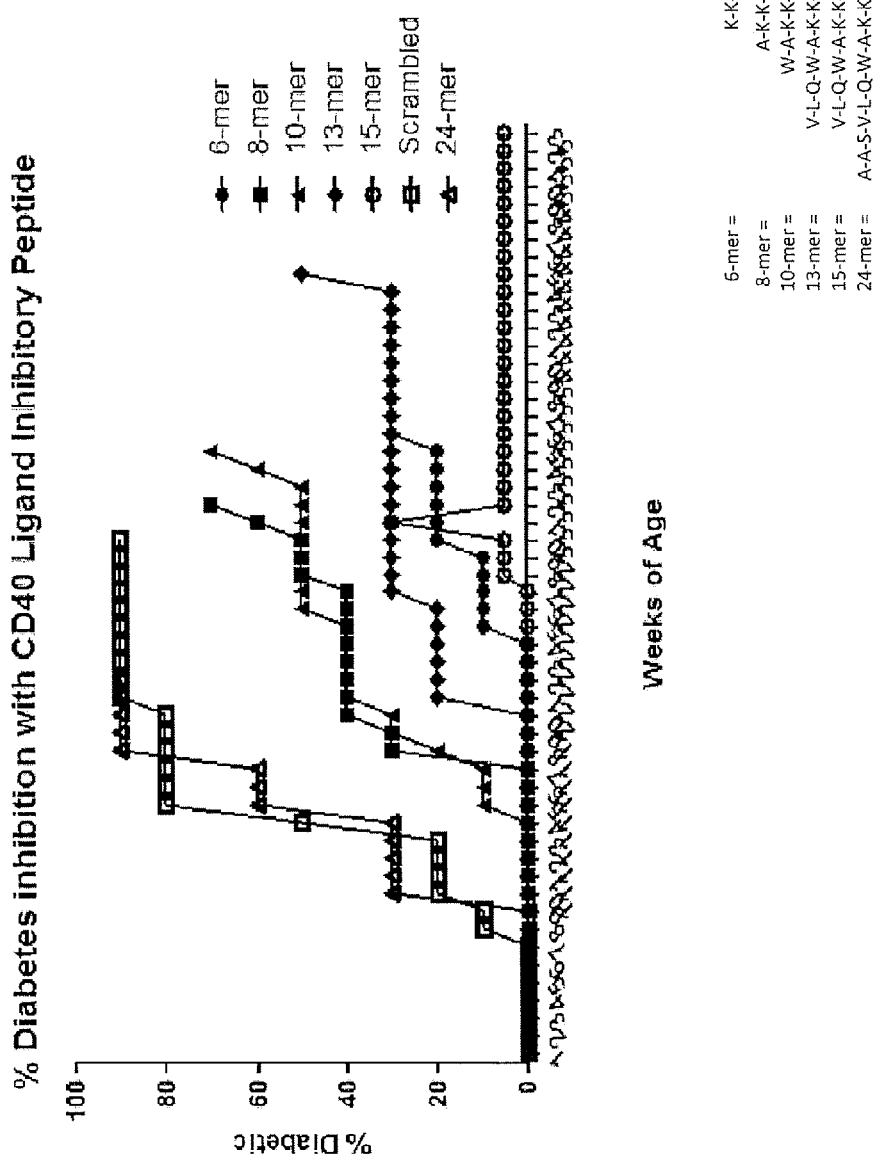
FIG. 1 Effect of various peptides of CD154 on the development of diabetes in NOD mice. The 6-mer (SEQ ID NO: 4), 8-mer (SEQ ID NO: 5), 10-mer (SEQ ID NO: 24), 13-mer (SEQ ID NO: 25), 15-mer (SEQ ID NO: 27), and 24-mer (SEQ ID NO: 26) were tested.

The present invention is based on the discovery that a unique subset of T-cells, which express CD40 protein, and thus are referred to as Th40 cells, is instrumental in autoimmune inflammation. Moreover, involvement of Th40 cells in the autoimmune process is dependent on the interaction between CD40 protein expressed on the surface of the T-cell, and CD154 protein. Interaction of CD40 and CD154 results in activation signals being delivered between the cells, and subsequent activation of the Th40 cell. Such activation results in propagation of the Th40 cell and an increase in inflammation (e.g., an increase in the number of immune cells and immunoregulatory molecules, present in the system). Accordingly, inhibition of the CD40/CD154 interaction may modulate Th40 cell activity, and thereby affect inflammation. Thus, the present invention relates to peptides that affect the interaction between a CD40 protein and a CD154 protein, thereby modulating inflammation. In particular, the present invention relates to peptides that affect the interaction between CD40 protein expressed on the surface of a T-cell, and a CD154 protein, thereby affecting T-cell activity and modulating inflammation. The invention also relates to methods of using such peptides to modulate inflammation and to treat autoimmune disease. The present invention also encompasses the use of such peptides to detect Th40 cells.

Before the present invention is further described, it is to be understood that this invention is not strictly limited to particular embodiments described, as such may of course vary. It is also to be understood that the terminology used herein is for the purpose of describing particular embodiments only, and is not intended to be limiting, since the scope of the present invention will be limited only by the claims.

It must be noted that as used herein and in the appended claims, the singular forms "a," "an," and "the" include plural referents unless the context clearly dictates otherwise. It should further be understood that as used herein, the term "a" entity or "an" entity refers to one or more of that entity. For example, a nucleic acid molecule refers to one or more nucleic acid molecules. As such, the terms "a", "an", "one or more" and "at least one" can be used interchangeably. Similarly, the terms "comprising", "including" and "having" can be used interchangeably.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments are specifically embraced by the present invention and are disclosed herein just as if each and every combination was individually and explicitly disclosed. In addition, all sub-combinations are also specifically embraced by the present invention and are disclosed herein just as if each and every such sub-combination was individually and explicitly disclosed herein.

It is further noted that the claims may be drafted to exclude any optional element. As such, this statement is intended to serve as antecedent basis for use of such exclusive terminology as "solely," "only" and the like in connection with the recitation of claim elements, or, use of a "negative" limitation.

Furthermore, as used herein the term animal refers to a vertebrate, preferably a mammal, more preferably a human. Suitable mammals on which to use the methods of the present invention include but are not limited farm animals, sports animals, pets, primates, mice, rats, horses, dogs, cats, and humans. The term animal can be used interchangeably with the terms subject or patient.

One embodiment of the present invention is a peptide that interacts with a CD40 protein in such a manner as to modulate inflammation. As used herein, the terms interact, interaction, and the like, mean that two molecules come into sufficient physical proximity such that they cause a modulation of inflammation. One type of interaction is a binding interaction. In such an interaction the peptide associates with CD40 to form a complex. An example of complex formation is the association of an antigen with an antibody. According to the present invention, binding of a peptide of the present invention to a CD40 protein can be reversible (e.g., non-covalent binding interactions) or non-reversible (e.g., covalent binding interactions). Moreover, a reversible interaction can be strong or weak, the strength of the interaction being determined by the forces (e.g., ionic charges, hydrogen binding, van der Walls interactions, etc.) exerted by each protein on the other protein in the complex. Factors affecting the strength of an interaction between two molecules are known to those skilled in the art. One useful measure of the strength of binding between two molecules, such as a peptide and a protein, is the dissociation constant (Kd). Preferred peptides of the present invention are those that bind to a CD40 protein with a Kd of no more than about $1\times10^{-6}$ M, about $1\times10^{-7}$ M, or about $1\times10^{-8}$ M. Particularly preferred peptides are those having a Kd of less than about $1\times10^{-9}$ M. In one embodiment, a peptide of the present invention binds to a CD40 protein with a Kd of less than 100 nM, less than 50 nM, less than 25 nM, less than 10 nM, less than 5 nM, less than 3 nM, less than 2 nM, or less than 1 nM. Methods of measuring and analyzing binding interactions between a peptide and a CD40 protein are known by those of skill in the art.

As used herein, to modulate inflammation means to change the level of Th40 cells present in an animal, or in a culture of T-cells. As used herein, the terms level, number, count and concentration can be used interchangeably. Modulation of inflammation can mean an increase or decrease in the number of Th40 cells present in the inflammatory environment. Consequently, modulation can be referred to as positive or negative. Positive modulation (also referred to as up-regulation) of inflammation refers to an increase in the number of Th40 cells in the inflammatory environment. Negative modulation (also referred to as down-regulation) of inflammation refers to a reduction in the number of Th40 cells present in the inflammatory environment. A preferred peptide is one that down-regulates inflammation, thereby reducing the number of Th40 cells present in the inflammatory environment. Positive and negative modulation of inflammation may or may not result in a change in the type and amount of immunoregulatory molecules present in the inflammatory environment.

It will be appreciated by those skilled in the art that both a cell culture system and the immune system of an animal comprise basal levels of immune cells and immunoregulatory molecules. The phrases basal level and normal level can be used interchangeably. With regard to the immune system of an animal, as used herein, the basal level of a type of immune cell (e.g., Th40 cell), or a immunoregulatory molecule, refers to the average number of that cell type, or immunoregulatory molecule, present in a population of individuals considered healthy (i.e., free of metabolic, autoimmune, or infectious disease). With regard to a cell culture system, as used herein, the basal level of a type of immune cell, or an immunoregulatory molecule, refers to the average level of that cell type, or immunoregulatory molecule, present in a population of cells that is non-activated. Those skilled in the art are capable of determining if a T-cell, or a population of such cells, is activated. For example, the expression of CD69, CD25 and/or CD154 proteins by a cell indicates that the cell has been activated.

The basal level of a cell or molecule can be a specific amount (e.g., a specific concentration) or it can encompass a range of amounts. Basal levels, or ranges, of immune cells and immunoregulatory molecules are known to those in the art. For example, in a healthy individual, the normal level of CD4+ T-cells present in human blood is 500-1500 cells/ml. Variability in this measurement can result from differences in the method used to determine the cell count. Furthermore, normal levels of cells can also be reported as a percentage of a total cell population. For example, in a healthy individual, Th40 cells make up less than 25% of the total T cell population. Thus, as used herein, the term inflammation refers to an inflammatory environment in which Th40 cells make up greater than about 25%, greater than about 30%, greater than about 35%, greater than about 40%, greater than about 45%, greater than about 50%, greater than about 55%, greater than about 60%, greater than about 65%, greater than about 70%, greater than about 75%, or greater than about 80% of the total T-cell population. Moreover, a preferred peptide of the present invention is one that reduces the level of Th40 cells to less than about 50%, less than about 45%, less than about 40%, less than about 35%, less than about 30%, less than about 27%, or equal to about 25% of the total T-cell population. Methods of measuring different types of T-cells in the T-cell population are known to those skilled in the art. Furthermore, a novel method for detecting Th40 cells using peptides of the present invention is disclosed herein.

As used herein, the phrase inflammatory environment refers to the overall population of immune cells, and related immunoregulatory molecules, that are present in a culture of cells, or in the body of an animal. As such, the phrase inflammatory environment encompasses the types, and/or the relative amounts of immune cells and immunoregulatory molecules (e.g., cytokines) present in a culture of cells, or in an animal, which are involved in affecting an inflammatory reaction. Examples of cells encompassed by the term inflammatory environment include, but are not limited to, T cells, neutrophils, macrophages, granulocytes, and the like. The inflammatory environment relates to cells and molecules that mediate both acute and chronic inflammation. It will be appreciated by those skilled in the art that the inflammatory environment refers to the system to which peptides of the present invention are administered. In one embodiment, the system is a cell culture system. In one embodiment, the system is a whole animal.

A preferred peptide of the present invention is one that selectively interacts with a CD40 protein in solution, as determined using an assay such as an immunosorbent assay, or on the surface of a T-cell. As used herein, the terms selectively, selective, specific, and the like, indicate the peptide has a greater affinity for a CD40 protein than it does for proteins unrelated to the CD40 protein. More specifically, the terms selectively, selective, specific, and the like indicate that the affinity of the peptide for CD40 is statistically significantly higher than its affinity for a negative control (e.g., an unrelated protein such as albumin) as measured using a standard assay (e.g., ELISA). Suitable techniques for assaying the ability of a peptide to selectively interact with a CD40 protein are known to those skilled in the art. Such assays can be in vitro or in vivo assays. Examples of useful assays include, but are not limited to, an enzyme-linked immunoassay, a competitive enzyme-linked immunoassay, a radioimmunoassay, a fluorescence immunoassay, a chemiluminescent assay, a lateral flow assay, a flow-through assay, an agglutination assay, a particulate-based assay (e.g., using particulates such as, but not limited to, magnetic particles or plastic polymers, such as latex or polystyrene beads), an immunoprecipitation assay, an immunoblot assay (e.g., a western blot), a phosphorescence assay, a flow-through assay, a chromatography assay, a polyacrylamide gel electrophoresis (PAGE)-based assay, a surface plasmon resonance assay, a spectrophotometric assay, a particulate-based assay, an electronic sensory assay and a flow cytometric assay. Methods of performing such assays are well known to those skilled in the art. In one embodiment, an assay can be performed using cells in culture, or it can be performed in a whole animal. Assays can be designed to give qualitative, quantitative or semi-quantitative results, depending on how they are used and the type of result that is desired.

One embodiment of the present developments is a peptide that interacts with a CD40 protein in such a manner as to affect the interaction of the CD40 protein with a CD154 protein, thereby modulating inflammation. The effect of the peptide on the CD40/CD154 interaction can be positive or it can be negative. For example, the peptide can interact with the CD40 protein in such a manner that the strength of the interaction between the CD40 protein and a CD154 protein is increased. Alternatively, the peptide can interact with the CD40 protein such that the strength of the interaction between the CD40 protein and a CD154 protein is decreased. Methods of measuring the strength of binding between the peptide and a CD40 protein are known to those skilled in the art. A preferred peptide of the present invention is one that reduces the strength of the interaction between a CD40 protein and a CD154 protein. Preferred peptides of the present invention reduce the strength of binding between a CD40 protein and a CD154 protein by at least 10%, at least 20%, at least 30%, at least 40%, at least 50%, at least 60%, at least 70%, at least 80%, at least 90%, or at least 95%. A particularly preferred peptide is one that completely inhibits binding of CD40 to CD154. Complete inhibition of binding between CD40 and CD154 means that when a peptide of the present invention is brought into proximity with a CD40 protein and a CD154 protein under conditions that would normally allow the interaction of CD40 and CD154, no such interaction occurs, and activation signals are not stimulated in the CD40-expressing cell. Consequently CD40/CD154 mediated modulation of inflammation does not occur. In one embodiment, the peptide interacts with the CD40 protein in such a manner as to reduce the level of inflammation in the system. In one embodiment, the peptide interacts with the CD40 protein in such a manner as to inhibit the development of inflammation in the system.

While peptides of the present invention can interact with any site on the CD40 protein, preferred peptides of the present invention interact with the CD40 protein at a location that overlaps with the CD154 binding site. In one embodiment, a peptide of the present invention interacts with the CD40 protein at the CD154 binding site. An example of such a peptide is a CD40 ligand competitive antagonist. As used herein, peptides that interfere with, or inhibit, the binding of a CD154 protein to a CD40 protein are referred to as small interfering peptides (SIPs). As used herein a small interfering peptide is a peptide that, through physio-chemical properties, interferes with the interaction of a CD40 protein with a CD154 protein, thereby preventing activation signals from being delivered to the CD40-bearing cell, thus limiting the activation of the CD40-bearing cell, and consequently, inflammation. As demonstrated herein, the consequences of such interference are prevention of T-cell activation and propagation, and a prevention or reduction of inflammation.

A peptide useful for practicing methods of the present developments should be of a size sufficient to interact with CD40 protein in such a manner as to modulate inflammation. It is understood by those skilled in the art that preferred peptides are relatively short since they are easier and less expensive to produce. Preferred peptides may be those that are less than 20 amino acids in length. A preferred peptide may be one that is 6, 13 or 15 amino acids in length. In one embodiment, the peptide consists of an amino acid selected from the group consisting of SEQ ID NO:4, SEQ ID NO:8, SEQ ID NO:9 and SEQ ID NO:10. The sequences of such peptides are shown below in Table 1.

TABLE 1

| SEQ ID NO | SEQUENCE | Description |
|---|---|---|
| 1 | MIETYSQPSP RSVATGLPAS MKIFMYLLTV FLITQMIGSV LFAVYLHRRL DKVEEEVNLH EDFVFIKKLK RCNKGEGSLS LLNCEEMRRQ FEDLVKDITL NKEEKKENSF EMQRGDEDPQ IAAHVVSEAN SNAASVLQWA KKGYYTMKSN LVMLENGKQL TVKREGLYYV YTQVTFCSNR EPSSQRPFIV GLWLKPSSGS ERILLKAANT HSSSQLCEQQ SVHLGGVFEL QAGASVFVNV TEASQVIHRV GFSSFGLLKL | SwissPro 27548.2 Mouse CD40 Ligand (CD154 Protein) |
| 2 | MIETYNQTSP RSAATGLPIS MKIFMYLLTV FLITQMIGSA LFAVYLHRRL DKIEDERNLH EDFVFMKTIQ RCNTGERSLS LLNCEEIKSQ FEGFVKDIML NKEETKKENS FEMQKGDQNP QIAAHVISEA SSKTTSVLQW AEKGYYTMSN NLVTLENGKQ LTVKRQGLYY IYAQVTFCSN REASSQAPFI ASLCLKSPGR FERILLRAAN THSSAKPCGQ QSIHLGGVFE LQPGASVFVN VTDPSQVSHG TGFTSFGLLK L | SwissPro 29965 Human CD40 Ligand (CD154 Protein) |
| 3 | KGYY | Core-sequence |
| 4 | KKGYYT | 6-mer |
| 5 | AKKGYYTM | 8-mer-mouse |
| 6 | AEKGYYTM | 8-mer human |
| 7 | VLQWAKKGYYTMKSK | 15-mer-mouse |
| 8 | VLQWAEKGYYTMSNN | 15-mer human |
| 9 | NAASVLQWAKKGYYTMKSNLVMLE | 24-mer |
| 10 | ISQAVHAAHAEINEAGR | 15-mer from ovalbumin; control peptide |
| 11 | G-L-Q-W-A-K-K-G-Y-Y-T-M-K-S-N | Gly-1 |
| 12 | V-G-Q-W-A-K-K-G-Y-Y-T-M-K-S-N | Gly-2 |
| 13 | V-L-G-W-A-K-K-G-Y-Y-T-M-K-S-N | Gly-3 |
| 14 | V-L-Q-G-A-K-K-G-Y-Y-T-M-K-S-N | Gly-4 |
| 15 | V-L-Q-W-G-K-K-G-Y-Y-T-M-K-S-N | Gly-5 |
| 16 | V-L-Q-W-A-G-K-G-Y-Y-T-M-K-S-N | Gly-6 |
| 17 | V-L-Q-W-A-K-G-G-Y-Y-T-M-K-S-N | Gly-7 |
| 18 | V-L-Q-W-A-K-K-G-G-Y-T-M-K-S-N | Gly-8 |
| 19 | V-L-Q-W-A-K-K-G-Y-G-T-M-K-S-N | Gly-9 |
| 20 | V-L-Q-W-A-K-K-G-Y-Y-G-M-K-S-N | Gly-10 |
| 21 | V-L-Q-W-A-K-K-G-Y-Y-T-G-K-S-N | Gly-11 |
| 22 | ISQAVHAAHAEINEAGR | 15-mer from ovalbumin; control peptide |
| 23 | YVQGKANLKSKLMYT | Scrambled peptide |

Interaction of a CD40 protein and a CD154 protein has been shown to occur at particular regions within each protein. The inventor has now shown that, surprisingly, a peptide comprising only a short portion of the CD154 region that interacts with CD40 is capable of binding to a CD40 protein, thereby modulating inflammation. Thus, one embodiment of the present invention is a peptide that comprises at least a portion of the amino acid sequence of a CD154 protein such that the peptide interacts with CD40 protein in such a manner as to modulate inflammation. In one embodiment, interaction of the peptide with CD40 protein results in negative modulation of inflammation. In one aspect, the peptide comprises at least a portion of SEQ ID NO:1 or SEQ ID NO:2. In a preferred aspect, the peptide is as short as possible yet comprises enough of the CD154 protein to allow interaction with a CD 40 protein in such a manner as to modulate inflammation. In one embodiment, a peptide of the present invention comprises 6, 13 or 15 contiguous amino acids from SEQ ID NO:1 or SEQ ID NO:2, and interacts with CD40 in such a manner as to modulate inflammation. A preferred peptide comprises a core sequence consisting of lysine-glycine-tyrosine-tyrosine (KGYY; SEQ ID NO:3), which corresponds to amino acids 142-145 of SEQ ID NO:1 and amino acids 143-146 of SEQ ID NO:2. Useful peptides can comprise additional regions of sequence from SEQ ID NO:1 or SEQ ID NO:2 that are adjacent to the core sequence, so long as the peptide is capable of modulating inflammation. In one embodiment of the present invention, a peptide comprises at least one sequence selected from the group consisting of SEQ ID NO:3, SEQ ID NO:4, SEQ ID NO:8, SEQ ID NO:9 and SEQ ID NO:10, so long as the peptide interacts with CD40 protein in such a manner as to modulate inflammation. In one embodiment of the present developments, a peptide consists of a sequence selected from the group consisting of SEQ ID NO:4, SEQ ID NO:8, SEQ ID NO:9 and SEQ ID NO:10.

While peptides of the present invention can consist entirely of sequences that are responsible for the interaction of the peptide with a CD40 protein, they may additionally contain amino acid sequences that do not interact with a CD40 protein, but which have other useful functions. Any useful, additional amino acid sequence can be added to the CD40-interacting sequence, so long as the additional sequences do not have an unwanted affect on the ability of the CD40 interacting sequence to interact with a CD40 protein. For example, in addition to the amino acid sequence responsible for interacting with a CD40 protein, a peptide of the present invention can contain amino acid sequences that are useful for visualizing or purifying the peptide. Such sequences act as labels (e.g., enzymes) or tags (antibody binding sites). Examples of such labels and tags include, but are not limited to, B-galactosidase, luciferase, glutathione-s-transferase, thioredoxin, HIS-tags, biotin tags, and fluorescent tags. Other useful sequences for labeling and tagging proteins are known to those of skill in the art.

Likewise, peptides of the present invention can be modified, so long as such modification does not significantly affect the ability of the peptide to modulate inflammation. Such modifications can be made, for example, to increase the stability, solubility or absorbability of the protein. Examples of such modifications include, but are not limited to pegylation, glycosylation and chemical modification of the peptide.

Peptides of the instant invention can be obtained from nature (e.g., obtained from plants, animals or microorganisms) or they can be produced in a laboratory (e.g., recombinantly or synthetically). Preferred peptides are those that are synthesized. Also encompassed are peptides that are combinations of natural and synthetic molecules. General methods for producing and isolating recombinant or synthetic peptides are known to those skilled in the art. It should be noted that, as used herein, an isolated, or biologically pure, molecule is one that has been removed from its natural milieu. As such the terms isolated, biologically pure, and the like, do not necessarily reflect the extent to which the protein has been purified.

As has been described herein, interaction of the CD40 protein and the CD154 protein are necessary for involvement of Th40 cells in autoimmune inflammation. Consequently, inhibition of the interaction between a CD40 and CD154 protein using peptides of the present invention is a useful method of affecting autoimmune inflammation. Thus, one embodiment of the present invention is a method to reduce the interaction between a CD40 protein and a CD154 protein comprising introducing into an environment containing a CD40 protein and a CD154 protein a peptide that interacts with the CD40 protein in such a manner as to reduce the interaction between the CD40 protein and the CD154 protein. In one aspect of the invention, the peptide reduces the interaction between the CD40 protein and the CD154 protein by at least 5%, at least 10%, at least 20%, at least 30%, at least 40%, at least 50%, at least 60%, at least 70%, at least 80%, at least 90%, or at least 95%. In one embodiment, the peptide reduces the interaction between the CD40 protein and the CD154 protein by a factor of at least 10, at least 100, at least 1,000, at least 10,000. Methods of measuring the strength of the interaction between the CD40 protein and the CD154 protein have been discussed previously, and are also know to those of skill in the art.

One embodiment of the present invention is a method to modulate inflammation comprising contacting a CD40 protein with a peptide that interacts to the CD40 protein in such a manner as to modulate inflammation. In one aspect of the invention, interaction of the peptide with the CD40 protein increases the number of Th40 cells by at least 5%, at least 10%, at least 20%, at least 30%, at least 40%, at least 50%, at least 60%, at least 70%, at least 80%, at least 90%, or at least 95%. In one embodiment, interaction of the peptide with the CD40 protein increases the number of Th40 cells by a factor of at least 10, at least 100, at least 1,000, at least 10,000. One aspect of the present invention is a method to reduce inflammation in a patient, the method comprising administering a peptide of the present invention to the patient. In one embodiment, the peptide comprises an amino acid sequence selected from the group consisting of SEQ ID NO:3, SEQ ID NO:4, SEQ ID NO:8, SEQ ID NO:9 and SEQ ID NO:10. In one embodiment, the peptide consists of an amino acid sequence selected from the group consisting of SEQ ID NO:4, SEQ ID NO:8, SEQ ID NO:9 and SEQ ID NO:10. In a preferred embodiment, interaction of the peptide with the CD40 protein decreases the number of Th40 cells by at least 5%, at least 10%, at least 20%, at least 30%, at least 40%, at least 50%, at least 60%, at least 70%, at least 80%, at least 90%, or at least 95%. In another embodiment, interaction of the peptide with the CD40 protein decreases the number of Th40 cells by a factor of at least 10, at least 100, at least 1,000, at least 10,000. In a preferred embodiment, the level of Th40 cells is reduced so that Th40 cells comprise no more than about 20%, about 25%, about 30%, about 35%, or about 40% of the total T-cell population.

Peptides and methods of the present invention are suitable for use in cell culture as well as for treating a patient. As used herein the term patient refers to any animal in need of such treatment. The animal can be a human or a non-human animal. A preferred animal to treat is a mammal. A peptide can be administered or applied per se, or as pharmaceutical compositions. A peptide of the present invention, or a pharmaceutical composition thereof, can be administered to a patient by a variety of routes, including, but limited to, by injection (e.g., intravenous, intramuscular, subcutaneous, intrathecal, intraperitoneal), by inhalation, by oral (e.g., in a pill, tablet, capsule, powder, syrup, solution, suspension, thin film, dispersion or emulsion), transdermal, transmucosal, pulmonary, buccal, intranasal, sublingual, intracerebral, intravaginal rectal or topical administration or by any other convenient method known to those of skill in the art.

The amount of a peptide of the present invention and/or a pharmaceutical composition thereof that will be effective can be determined by standard clinical techniques known in the art. Such an amount is dependent on, among other factors, the patient being treated, including, but not limited to the weight, age, and condition of the patient, the intended effect of the compound, the manner of administration and the judgment of the prescribing physician. A peptide of the present invention, or a pharmaceutical composition thereof, can be administered alone or in combination with one or more other pharmaceutical agents, including other compounds of the present invention. The specific pharmaceutical composition depends on the desired mode of administration, as is well known to the skilled artisan.

Because the inventors have discovered that Th40 cells are intimately involved in the development of autoimmune diseases, the peptides and methods disclosed herein can be used to affect inflammation resulting from such diseases. Thus, one embodiment of the present invention is a method to treat autoimmune disease in a patient in need of such treatment, the method comprising administering to a patient a peptide that interacts with the CD40 protein, thereby reducing inflammation. In one embodiment the peptide interacts with the CD40 protein in such a manner as to affect the interaction of CD40 and CD154, thereby reducing inflammation. In a preferred embodiment, interaction of the peptide with the CD40 protein reduces the number of Th40 cells in a patient to a level equal to that observed in subjects that do not have autoimmune disease. The present invention is suitable for treating any patient having an autoimmune disease the development of which is dependent on Th40 cells. More specifically, peptides of the present invention are suitable for reducing the level of Th40 cells in such patients. In a preferred embodiment, a peptide of the present invention reduces the level of Th40 cells in a patient suffering from an autoimmune disease to no more than about 25% of the total T-cell population. Examples of such disease include, but are not limited to, asthma, type 1 diabetes; multiple sclerosis; systemic lupus erythematosa; rheumatoid arthritis; Crohn's disease; inflammatory bowel disease; chronic obstructive pulmonary disease (COPD) including types of autoimmune asthma; atherosclerosis; vasculitis; hypertension; thyroiditis including Hashimoto's and Graves diseases; primary biliary cirrhosis; Paget's disease; Addison's disease; acute respiratory distress syndrome, acute lung injury; ACI associated with organ transplantation; hypertension, etc.

One example of a disease that is particularly amenable to treatment using a peptide of the present invention is diabetes. In diabetes, the body's production of, or response to, insulin is impaired. Consequently, cells are unable to utilize glucose in the blood, and the levels of this sugar become elevated. Mice are considered diabetic when their blood glucose level is greater than 250 mg/dl for three consecutive days. In humans, a normal, average blood glucose level is 60-110 mg/dl. However, diabetics have blood glucose levels of at least 130 mg/dl, and usually much higher. Thus, one embodiment of the present invention is a method to prevent diabetes in an individual at risk for developing diabetes, the method comprising administering to the individual a peptide of the present invention. Such risk can result from familial factors (e.g., inheritance) or from other factors, such as the physical condition of the individual. Methods of risk assessment are known to those skilled in the art. In one embodiment, the peptide is administered at a time when the individual's blood glucose level is from about 60 mg/dl to about 110 mg/dl. In one embodiment, the peptide comprises an amino acid sequence selected from the group consisting of SEQ ID NO:3, SEQ ID NO:4, SEQ ID NO:8, SEQ ID NO:9 and SEQ ID NO:10, so long as the peptide can downregulate inflammation. In one embodiment, the peptide consists of an amino acid sequence selected from the group consisting of SEQ ID NO:3, SEQ ID NO:4, SEQ ID NO:8, SEQ ID NO:9 and SEQ ID NO:10.

The inventors have also shown that, surprisingly, peptide of the present developments can be used to reverse the disease process in individuals already showing signs of diabetes. Thus, one aspect of the present developments is a method to reverse diabetes comprising administering to a patient diagnosed as having diabetes, a peptide of the present developments. In one embodiment, the peptide comprises an amino acid sequence selected from the group consisting of SEQ ID NO:3, SEQ ID NO:4, SEQ ID NO:8, SEQ ID NO:9 and SEQ ID NO:10, so long as the peptide can downregulate inflammation. In one embodiment, the peptide consists of an amino acid sequence selected from the group consisting of SEQ ID NO:3, SEQ ID NO:4, SEQ ID NO:8, SEQ ID NO:9 and SEQ ID NO:10. As used herein the phrase to reverse diabetes means to reduce the blood glucose level of a diabetic individual to a level comparable to that observed in a non-diabetic individual. As noted above, the blood glucose level of a non-diabetic subject is from about 60 mg/dl to about 110 mg/dl. Thus, one aspect of the present invention is a method to reduce the blood glucose level in a patient diagnosed as having diabetes to less than 110 mg/dl, and preferably between 60 mg/dl and 110 mg/dl.

As has been described, peptides of the present developments selectively bind to a CD40 expressing cell. Consequently, peptides of the present invention may be used to identify Th40 cells. Thus, one embodiment of the present invention is a method to detect Th40, said method comprising contacting a T-cell population with a peptide of the present invention. In a preferred embodiment, the peptide is labeled with a detectable marker, such as, for example, luciferase or alkaline phosphatase. Such detection can be performed using assay techniques known to those skilled in the art. In general, an assay for detecting Th40 cells using a peptide of the present invention comprises (a) obtaining a sample of cells; (b) contacting a peptide of the present invention with said cells under condition suitable to allow binding of the peptide to Th40 cells, if present; (c) washing said cells using conditions that disrupt non-specific interactions, and that remove unbound peptide; and (d) detecting peptide bound to cells. Detection of bound peptide can be achieved directly or indirectly. For example, direct detection can be achieved using a peptide labeled using a detectable marker, as disclosed herein. Following the wash step listed above, the cells are then simply screened for the presence of detectable marker. The presence of detectable marker in the cell sample indicates the presence of Th40 cells. Alternatively, indirect detection involves the use of a second molecule, such as an antibody, that binds to the peptide. In an indirect detection assay, following the wash step listed above, a detection molecule that binds the peptide is added to the cell sample. The detection molecule is labeled with a detectable marker. After washing away unbound detection molecule, the cells are screened for the presence of detectable marker. The presence of detectable marker in the cell sample indicates the presence of Th40 cells. It should be understood that the assays described herein are meant as examples of useful assays, and other assay techniques can be employed. Suitable assay techniques are known to those skilled in the art, and are also disclosed in, for example, Molecular Cloning: A Laboratory Manual, Sambrook, J., Fritsch, E. F., and Maniatis, T, Cold Spring Harbor Laboratory Press; 2nd Edition (December 1989). All referenced cited herein are incorporated herein in their entirety.

The assay technology described above can also be used to identify other molecules that affect the interaction of a CD40 protein with a CD514 protein. Examples of such molecules include, but are not limited to, proteins, peptides and small molecules. For example, assays can be designed that test the ability of molecules to compete with a peptide of the present invention for binding to a Th40 cell. For instance, a peptide labeled with a detectable marker, can be mixed with a test molecule and a population of cells known to contain Th40 cells, under conditions that allow binding of the peptide to the Th40 cells. Following an appropriate incubation period, the cells are washed to remove unbound peptide, and the cells screened for the presence of detectable marker. Alternatively, the labeled peptide could be bound to Th40 cells first, and after a wash step to remove unbound peptide, the test molecule could be added to the cells containing bound peptide. Following an incubating period and a wash step to remove unbound molecule, or released peptide, the cells are screened for the presence of detectable marker. In either case, absence of the detectable marker in the cell sample indicates the test molecule is able to compete with the peptide for binding to the Th40 cells, while presence of the detectable marker would indicate the test molecule does not inhibit binding of the peptide to Th40 cells. Inhibition of binding need not be 100%, as such assay would also be useful for identifying molecules that partially inhibit binding of the peptide to Th40 cells. It is understood by those skilled in the art that such assays would involve the use of positive controls (e.g., unlabeled peptide) and negative controls (e.g., a protein/molecule that is known not to bind to Th40 cells).

Because increased levels of Th40 cells are associated with the development of autoimmune disease, the present invention can be used to identify patients at risk for developing autoimmune disease. Thus, one embodiment of the present invention is a method to identify a patient at risk for developing an autoimmune disease. In one embodiment, patients at risk for developing an autoimmune disease are identified by obtaining a sample from a patient to be tested, contacting the T-cell portion said sample with a peptide of the present invention, and determining the level of Th40 cells present in the sample, wherein a level of Th40 cells greater than about 25% of the total T-cell population indicates the patient is at risk for developing an autoimmune disease. In one embodiment, the peptide comprises an amino acid sequence selected from the group consisting of SEQ ID NO:3, SEQ ID NO:4, SEQ ID NO:8, SEQ ID NO:9 and SEQ ID NO:10, so long as the peptide binds to the CD40 protein. In one embodiment, the peptide consists of an amino acid sequence selected from the group consisting of SEQ ID NO:3, SEQ ID NO:4, SEQ ID NO:8, SEQ ID NO:9 and SEQ ID NO:10. In a preferred embodiment the peptide is labeled with a suitable detectable marker such as, for example, luciferase or alkaline phosphatase.

The present invention also comprises kits useful for practicing the methods disclose herein. One embodiment is a kit for modulating inflammation in an animal or in cells in culture, the kit comprising a peptide that interacts with a CD40 protein in such a manner as to modulate inflammation. In one embodiment, the peptide comprises an amino acid sequence selected from the group consisting of SEQ ID NO:3, SEQ ID NO:4, SEQ ID NO:8, SEQ ID NO:9 and SEQ ID NO:10, so long as the peptide can down-regulate inflammation. In one embodiment, the peptide consists of an amino acid sequence selected from the group consisting of SEQ ID NO:3, SEQ ID NO:4, SEQ ID NO:8, SEQ ID NO:9 and SEQ ID NO:10. Another embodiment is a kit for determining the level of Th40 cells, the kit comprising a peptide that interacts with a CD40 protein, and means for detecting CD40-bound peptide. Kits can also contain associated reagents and components, such as, but not limited to, buffers, labels, containers, inserts, tubing, vials, syringes, and the like.

The following examples are provided for the purpose of illustration and are not intended to limit the scope of the present invention.

EXAMPLES

Example 1

This Example demonstrates the effect of various peptide fragments of CD154 on CD4/CD8 ratios and the development of diabetes in NOD mice.

Figure 2:
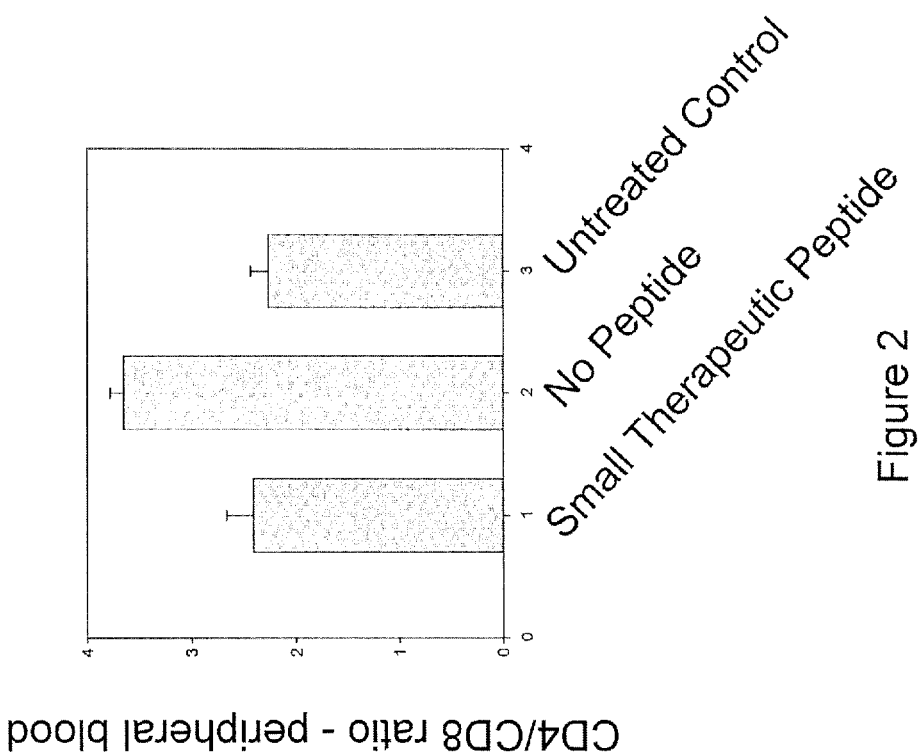
FIG. 2 shows the effect of a 15-mer peptide from CD154 on the CD4/CD8 ration in NOD mice.

Peptides were designed based on the amino acid sequence of mouse CD154 protein (SEQ ID NO:1) in the SwissPro database. The peptides were then ordered from New England Peptide. The lyophilized peptides were suspended in sterile saline at 1 mg/ml. 100 ug of a specified peptide was then injected into the tail vein of 8-9 week-old NOD mice. Control mice received 100 ul of sterile saline. This is well before the onset of diabetes, but after damage to pancreatic islets has begun. Three days after the initial injection, another 100 ug of peptide (or 100 ul of saline in the case of the Control mice) was injected into the tail vein. Mice were then injected with peptide (or saline) on a weekly basis. At 10 weeks of age, mice were monitored for diabetes, as indicated by a blood glucose level greater than 250 mg/dL for three consecutive days. The results of this study are shown in FIG. 1. During this time, blood was also taken from the tail vein, or by sub-mandibular venal puncture, and the level of CD4+ and CD8+ cells determined by flow cytometry using antibodies for CD4 protein and CD8 protein. The results of this analysis are shown in FIG. 2.

The results demonstrate that treatment with a peptide unrelated to the CD154 protein did not reduce the development of diabetes in NOD mice. In contrast, treatment of mice with a 15-mer peptide derived from the CD154 protein prevented the onset of diabetes. Further, both the 6-mer and 10-mer peptides derived from the CD154 protein had significant effects on the development of diabetes. In addition, the data demonstrate that the 15-mer peptide did not result in compromise of the immune system, as determined by the CD4/CD8 ratio.

Example 2

This Example demonstrates the effect of the 15-mer peptide on hyperglycemia in newly diabetic NOD mice.

Figure 3:
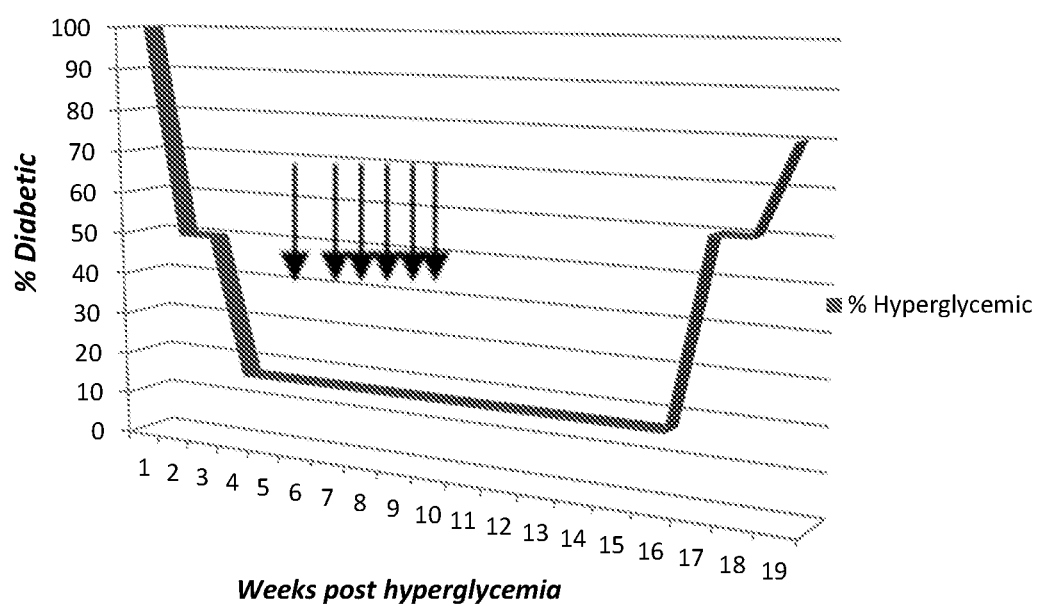
FIG. 3 provides data demonstrating the reversal of diabetes in NOD mice using a 15-mer peptide from CD154.

Six mice from that had received the 6-mer peptide in Example 1, and that had subsequently developed diabetes, were injected intravenously with 100 ug of the 15-mer peptide. These mice were then given weekly injections of the 15-mer peptide into their tail veins, and their blood glucose levels monitored twice-weekly. The 15-mer peptide was administered for a total of ten weeks, after which the treatment was stopped. The results of this study are shown in FIG. 3.

This study demonstrates that injection of the 15-mer peptide into already diabetic mice can reverse hyperglycemia. It also demonstrates that cessation of the treatment results in return of hyperglycemia within 7 weeks.

Example 3

This study demonstrates the ability of the 15-mer peptide to bind to Th40 cell and B cells.

Figure 4:
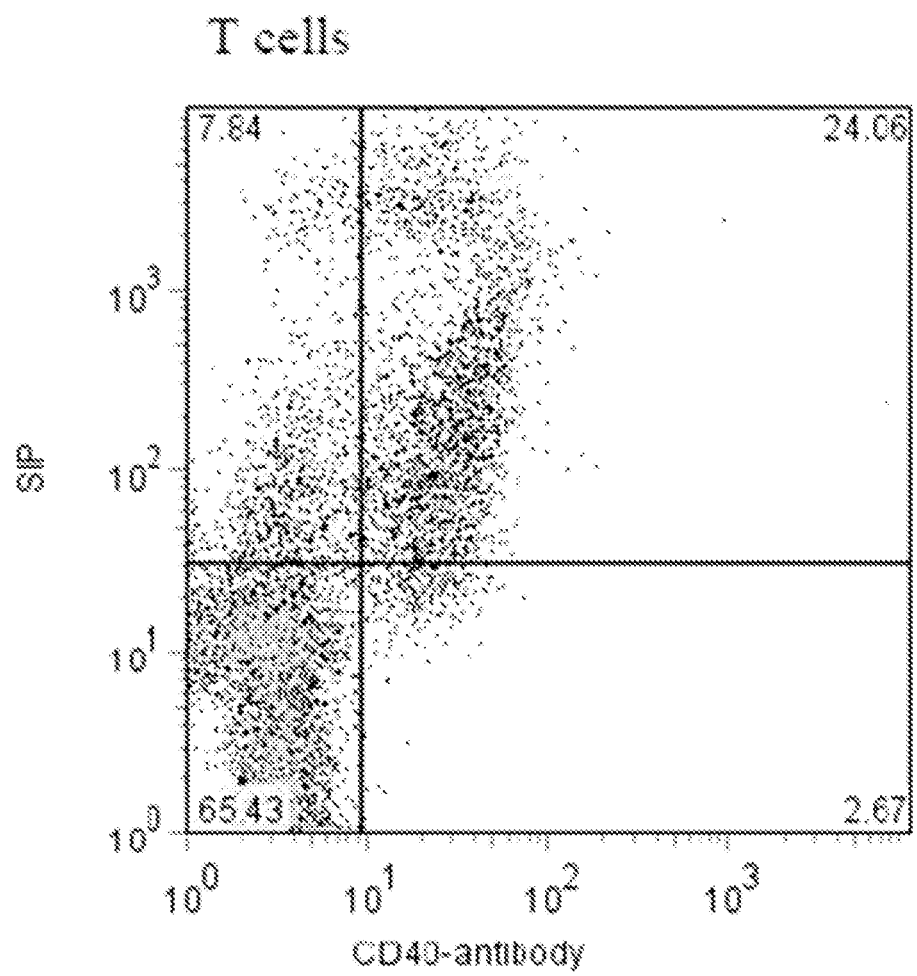
FIG. 4 demonstrates the detection of Th40 cells using a 15-mer peptide from CD154.

Total lymphocytes were isolated from 9 week-old NOD mice. The lymphocytes were incubated with anti-CD, anti-CD8, and an FITC-labeled 15-mer peptide, and then analyzed by flow cytometry. Cells were gated for CD4 (both CD4hi and CD4lo populations were included) and CD4 versus the 15-mer peptide. The results of this analysis are shown in FIG. 4.

Figure 5:
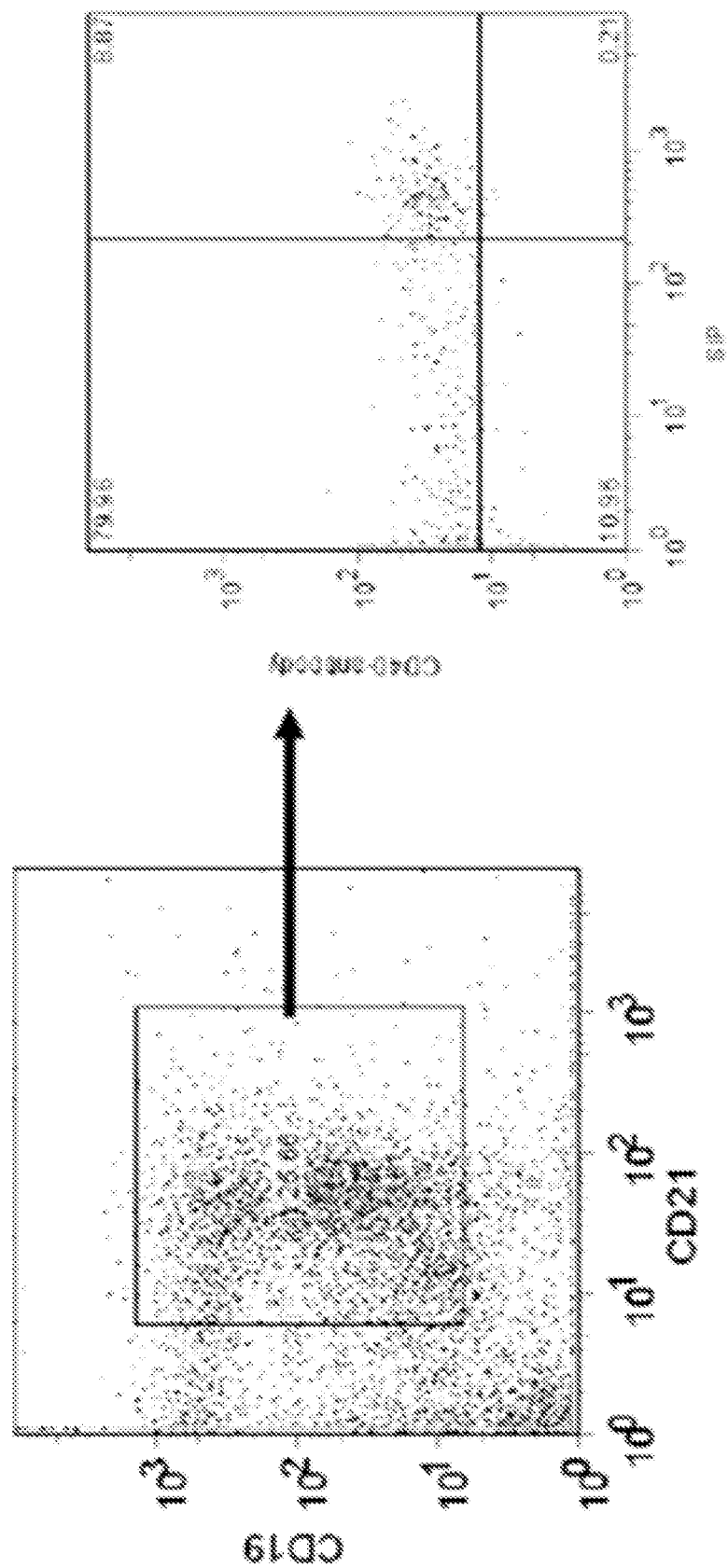
FIG. 5 provides data demonstrating the screening of B cells using a 15-mer peptide from CD154.

B cells were isolated from the spleens of NOD mice. Sorted MHC-II+ (major histocompatibility complex) cells were purified from total lymphocytes. Cells were stained with FITC-labeled 15 mer peptide, anti-CD40, and B cell markers CD19 and CD21. MHC-II+ cells were gated for CD19+ and CD21+ and then 15-mer peptide versus Cd40 antibody was measured. The results of this study are shown in FIG. 5.

This study shows that a substantial majority, 90% of CD40+ T-cells, also bind the 15-mer peptide, thereby demonstrating that the 15-mer peptide is highly specific for CD40+ cells. It also shows that while 90% of B cells were CD40 positive, only 8% of B cells bound the 15-mer peptide.

Example 4

This example demonstrates the level of CD40 positive cells in the blood of type-I diabetic subjects and non-diabetic (control) subjects.

Figure 6:
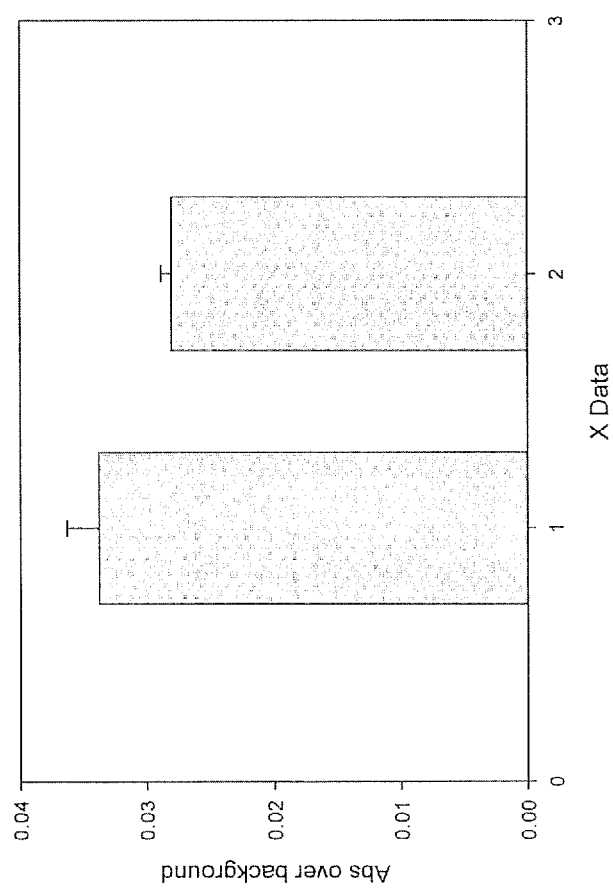
FIG. 6 shows a comparison of Th40 cell levels in diabetic and non-diabetic mice.

1 ml of whole blood was obtained from each individual and incubated with biotin-conjugated, 15-mer peptide. The cells were then exposed to horse radish peroxidase (HRP)-avidin, washed and the absorbance at 405 nm determined using a spectrophotometer. The results of this study are shown in FIG. 6.

This study demonstrates that blood cells from patients having type-I diabetes had higher 15-mer peptide binding activity than cells from non-diabetic controls.

Example 5

This example demonstrates the level of insulin granulation observed in the pancreas of NOD mice treated with either the 15-mer peptide or a peptide from ovalbumin.

Figure 7:
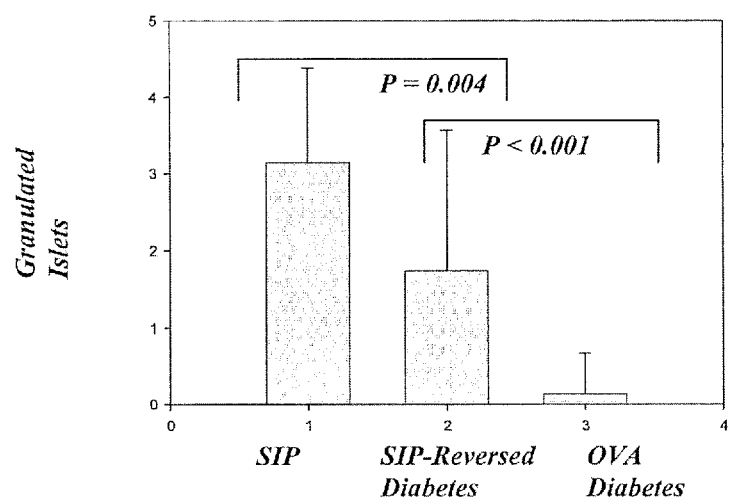
FIG. 7. shows the effect of treatment with the 15-mer peptide on insulin granulation of the pancreas.
Figure 8:
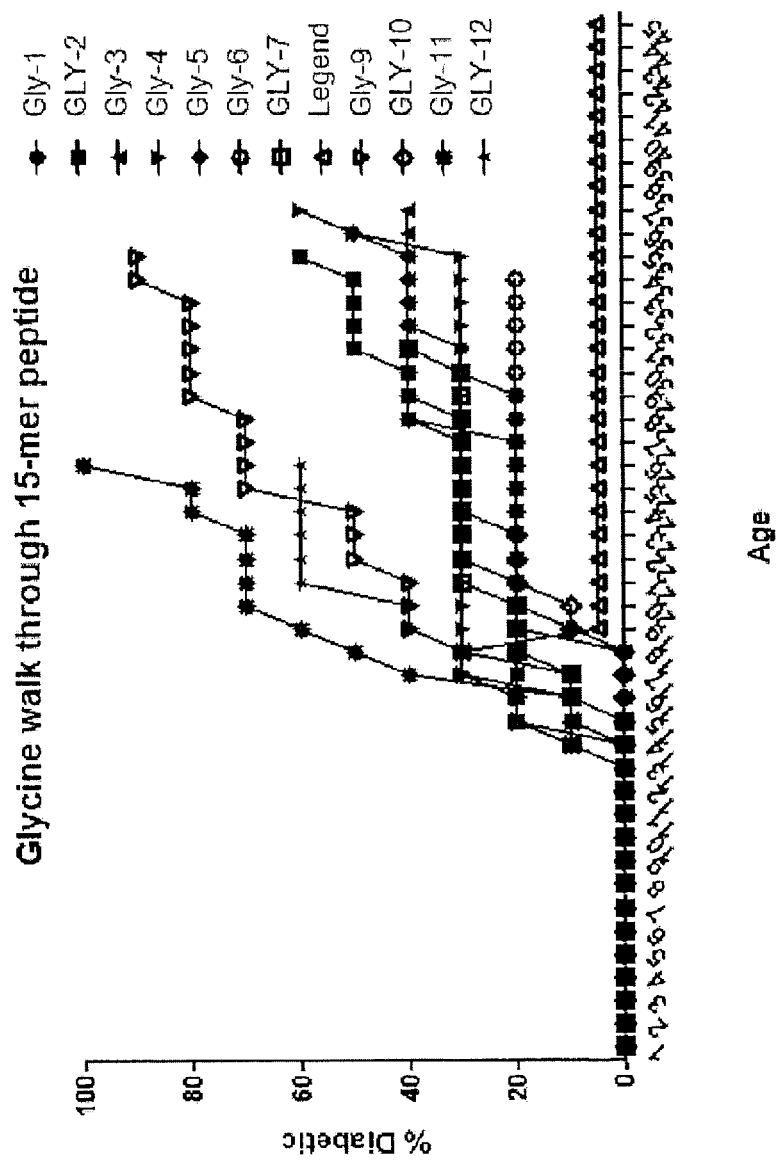
FIG. 8. Shows the effect of mutations in the 15-mer peptide on the ability of the 15-mer peptide to inhibit development of diabetes in NOD mice.

At the onset of diabetes, six NOD mice were injected with 100 ug/ml of the 15-mer peptide (SEQ ID NO:9), resulting in the reversal of hyperglycemia in 80% of the recipients. Six weeks after reversal of hyperglycemia, mice were sacrificed, and the pancreas removed for analysis. The pancreas was fixed, sectioned and then stained using an aldehyde/ fuschsin stain that allows detection of insulin granules. Granulation of the tissue was scored as follows: 4=completely granulated; 3=75% of islet granulated; 2=50% of islet granulated, and peri-insulitis; 1=25% of islet granulated; 0=no insulin granules detected. The results of this analysis are shown in FIG. 7.

This analysis demonstrates that the 15-mer peptide preserved insulin granules in the majority of the mice and was significantly improved in peptide-reversed diabetic mice compared to diabetic mice that received an irrelevant peptide.

Example 6

This example demonstrates the effect of mutations in the 15-mer peptide on its ability to prevent the onset of diabetes.

Peptide were designed and produced as described in Example 1. Variant peptides were produced so that in each variant, a glycine was substituted for an amino acid corresponding to an amino acid in positions 1-9 of SEQ ID NO:9, as follows:

```
Gly-1    G-L-Q-W-A-K-K-G-Y-Y-T-M-K-S-N    (SEQ ID NO: 11)

Gly-2    V-G-Q-W-A-K-K-G-Y-Y-T-M-K-S-N    (SEQ ID NO: 12)

Gly-3    V-L-G-W-A-K-K-G-Y-Y-T-M-K-S-N    (SEQ ID NO: 13)

Gly-4    V-L-Q-G-A-K-K-G-Y-Y-T-M-K-S-N    (SEQ ID NO: 14)

Gly-5    V-L-Q-W-G-K-K-G-Y-Y-T-M-K-S-N    (SEQ ID NO: 15)

Gly-6    V-L-Q-W-A-G-K-G-Y-Y-T-M-K-S-N    (SEQ ID NO: 16)

Gly-7    V-L-Q-W-A-K-G-G-Y-Y-T-M-K-S-N    (SEQ ID NO: 17)

Gly-9    V-L-Q-W-A-K-K-G-G-Y-T-M-K-S-N    (SEQ ID NO: 18)

Gly-10   V-L-Q-W-A-K-K-G-Y-G-T-M-K-S-N    (SEQ ID NO: 19)

Gly-11   V-L-Q-W-A-K-K-G-Y-Y-G-M-K-S-N    (SEQ ID NO: 20)

Gly-12   V-L-Q-W-A-K-K-G-Y-Y-T-G-K-S-N    (SEQ ID NO: 21)
```

NOD mice were placed in groups of 10, and the mice in each group injected IV weekly with 50 ug of either wild-type (WT; Legend) peptide or a variant peptide (in PBD, ph 7.2) listed above. The development of diabetes was monitored by measuring blood glucose levels on a weekly basis. Mice were considered "diabetic" when blood glucose was 250 mg/dl or greater for 2 consecutive readings. Injections began at 6 weeks of age=pre-diabetes.

This example demonstrates that substitution of a glycine at any of positions 1-7, or 9-12, reduces the ability of the 15-mer peptide to inhibit the development of diabetes. It also shows that such mutations do not completely abolish the ability of the mutated 15-mer peptide to inhibit the development of diabetes.

What is claimed is:

1. A peptide of 15 amino acids in length comprising a sequence of SEQ ID NO: 27.

2. The peptide of claim 1, wherein said peptide binds to CD40 proteins with a Kd of greater than $10^6$.

3. The peptide of claim 1, wherein said peptide binds to CD40.

4. The peptide of claim 1, wherein said peptide inhibits the binding of CD40 to CD154.

5. The peptide of claim 1, wherein said peptide binds CD40 at the site where CD40 interacts with CD154.

6. The peptide of claim 1, wherein said peptide inhibits the expansion of Th40 cells.

7. The peptide of claim 1, wherein said peptide reduces the number of Th40 cells.

8. The peptide of claim 1, wherein said peptide alters the cytokine expression profile of a cell population treated with said peptide.

9. A method for reducing the number of Th40 cells in a patient comprising administering to the patient a peptide of claim 1 that inhibits the interaction of CD40 and CD154.

10. An in vitro method to inhibit the interaction between a CD40 protein and a CD154 protein comprising contacting the CD40 protein with a peptide of claim 1.

11. The peptide of claim 1, wherein the peptide is pegylated.

12. The peptide of claim 1, wherein the peptide is glycosylated.

13. The peptide of claim 1, wherein the peptide comprises a chemical modification.

14. A method of inhibiting the interaction between a CD40 protein and a CD154 protein comprising contacting the CD40 protein with a peptide of claim 1 that binds to said CD40 protein at the CD154-binding site, thereby inhibiting the interaction of said CD40 ad CD154 proteins.

* * * * *

SEQUENCE LISTING

```
<160> NUMBER OF SEQ ID NOS: 27

<210> SEQ ID NO 1
<211> LENGTH: 260
<212> TYPE: PRT
<213> ORGANISM: Mus musculus

<400> SEQUENCE: 1

Met Ile Glu Thr Tyr Ser Gln Pro Ser Pro Arg Ser Val Ala Thr Gly
1               5                   10                  15

Leu Pro Ala Ser Met Lys Ile Phe Met Tyr Leu Leu Thr Val Phe Leu
            20                  25                  30

Ile Thr Gln Met Ile Gly Ser Val Leu Phe Ala Val Tyr Leu His Arg
        35                  40                  45

Arg Leu Asp Lys Val Glu Glu Glu Val Asn Leu His Glu Asp Phe Val
    50                  55                  60

Phe Ile Lys Lys Leu Lys Arg Cys Asn Lys Gly Glu Gly Ser Leu Ser
65                  70                  75                  80

Leu Leu Asn Cys Glu Glu Met Arg Arg Gln Phe Glu Asp Leu Val Lys
                85                  90                  95

Asp Ile Thr Leu Asn Lys Glu Glu Lys Lys Glu Asn Ser Phe Glu Met
            100                 105                 110

Gln Arg Gly Asp Glu Asp Pro Gln Ile Ala Ala His Val Val Ser Glu
        115                 120                 125

Ala Asn Ser Asn Ala Ala Ser Val Leu Gln Trp Ala Lys Lys Gly Tyr
    130                 135                 140

Tyr Thr Met Lys Ser Asn Leu Val Met Leu Glu Asn Gly Lys Gln Leu
145                 150                 155                 160

Thr Val Lys Arg Glu Gly Leu Tyr Tyr Val Tyr Thr Gln Val Thr Phe
                165                 170                 175

Cys Ser Asn Arg Glu Pro Ser Ser Gln Arg Pro Phe Ile Val Gly Leu
            180                 185                 190

Trp Leu Lys Pro Ser Ser Gly Ser Glu Arg Ile Leu Leu Lys Ala Ala
        195                 200                 205

Asn Thr His Ser Ser Ser Gln Leu Cys Glu Gln Gln Ser Val His Leu
    210                 215                 220

Gly Gly Val Phe Glu Leu Gln Ala Gly Ala Ser Val Phe Val Asn Val
225                 230                 235                 240

Thr Glu Ala Ser Gln Val Ile His Arg Val Gly Phe Ser Ser Phe Gly
                245                 250                 255

Leu Leu Lys Leu
            260

<210> SEQ ID NO 2
<211> LENGTH: 261
<212> TYPE: PRT
<213> ORGANISM: Homo sapiens

<400> SEQUENCE: 2
```

```
Met Ile Glu Thr Tyr Asn Gln Thr Ser Pro Arg Ser Ala Ala Thr Gly
1               5                   10                  15

Leu Pro Ile Ser Met Lys Ile Phe Met Tyr Leu Leu Thr Val Phe Leu
                20                  25                  30

Ile Thr Gln Met Ile Gly Ser Ala Leu Phe Ala Val Tyr Leu His Arg
            35                  40                  45

Arg Leu Asp Lys Ile Glu Asp Glu Arg Asn Leu His Glu Asp Phe Val
        50                  55                  60

Phe Met Lys Thr Ile Gln Arg Cys Asn Thr Gly Glu Arg Ser Leu Ser
65                  70                  75                  80

Leu Leu Asn Cys Glu Glu Ile Lys Ser Gln Phe Glu Gly Phe Val Lys
                85                  90                  95

Asp Ile Met Leu Asn Lys Glu Glu Thr Lys Lys Glu Asn Ser Phe Glu
            100                 105                 110

Met Gln Lys Gly Asp Gln Asn Pro Gln Ile Ala Ala His Val Ile Ser
        115                 120                 125

Glu Ala Ser Ser Lys Thr Thr Ser Val Leu Gln Trp Ala Glu Lys Gly
130                 135                 140

Tyr Tyr Thr Met Ser Asn Asn Leu Val Thr Leu Glu Asn Gly Lys Gln
145                 150                 155                 160

Leu Thr Val Lys Arg Gln Gly Leu Tyr Tyr Ile Tyr Ala Gln Val Thr
                165                 170                 175

Phe Cys Ser Asn Arg Glu Ala Ser Ser Gln Ala Pro Phe Ile Ala Ser
            180                 185                 190

Leu Cys Leu Lys Ser Pro Gly Arg Phe Glu Arg Ile Leu Leu Arg Ala
        195                 200                 205

Ala Asn Thr His Ser Ser Ala Lys Pro Cys Gly Gln Gln Ser Ile His
210                 215                 220

Leu Gly Gly Val Phe Glu Leu Gln Pro Gly Ala Ser Val Phe Val Asn
225                 230                 235                 240

Val Thr Asp Pro Ser Gln Val Ser His Gly Thr Gly Phe Thr Ser Phe
                245                 250                 255

Gly Leu Leu Lys Leu
            260

<210> SEQ ID NO 3
<211> LENGTH: 4
<212> TYPE: PRT
<213> ORGANISM: Mus musculus

<400> SEQUENCE: 3

Lys Gly Tyr Tyr
1

<210> SEQ ID NO 4
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 4

Lys Lys Gly Tyr Tyr Thr
1               5

<210> SEQ ID NO 5
<211> LENGTH: 8
```

```
<212> TYPE: PRT
<213> ORGANISM: Artificial Sequence
<220> FEATURE:
<223> OTHER INFORMATION: Synthetic Peptide

<400> SEQUENCE: 5

Ala Lys Lys Gly Tyr Tyr Thr Met
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 6

Ala Glu Lys Gly Tyr Tyr Thr Met
1               5

<210> SEQ ID NO 7
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 7

Val Leu Gln Trp Ala Lys Lys Gly Tyr Tyr Thr Met Lys Ser Lys
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 8

Val Leu Gln Trp Ala Glu Lys Gly Tyr Tyr Thr Met Ser Asn Asn
1               5                   10                  15

<210> SEQ ID NO 9
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 9

Asn Ala Ala Ser Val Leu Gln Trp Ala Lys Lys Gly Tyr Tyr Thr Met
1               5                   10                  15

Lys Ser Asn Leu Val Met Leu Glu
            20

<210> SEQ ID NO 10
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 10

Ile Ser Gln Ala Val His Ala Ala His Ala Glu Ile Asn Glu Ala Gly
1               5                   10                  15

Arg
```

<210> SEQ ID NO 11
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 11

Gly Leu Gln Trp Ala Lys Lys Gly Tyr Tyr Thr Met Lys Ser Asn
1               5                   10                  15

<210> SEQ ID NO 12
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 12

Val Gly Gln Trp Ala Lys Lys Gly Tyr Tyr Thr Met Lys Ser Asn
1               5                   10                  15

<210> SEQ ID NO 13
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 13

Val Leu Gly Trp Ala Lys Lys Gly Tyr Tyr Thr Met Lys Ser Asn
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 14

Val Leu Gln Gly Ala Lys Lys Gly Tyr Tyr Thr Met Lys Ser Asn
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 15

Val Leu Gln Trp Gly Lys Lys Gly Tyr Tyr Thr Met Lys Ser Asn
1               5                   10                  15

<210> SEQ ID NO 16
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 16

Val Leu Gln Trp Ala Gly Lys Gly Tyr Tyr Thr Met Lys Ser Asn
1               5                   10                  15

<210> SEQ ID NO 17
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 17

```
Val Leu Gln Trp Ala Lys Gly Gly Tyr Tyr Thr Met Lys Ser Asn
1               5                   10                  15
```

<210> SEQ ID NO 18
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 18

```
Val Leu Gln Trp Ala Lys Lys Gly Gly Tyr Thr Met Lys Ser Asn
1               5                   10                  15
```

<210> SEQ ID NO 19
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 19

```
Val Leu Gln Trp Ala Lys Lys Gly Tyr Gly Thr Met Lys Ser Asn
1               5                   10                  15
```

<210> SEQ ID NO 20
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 20

```
Val Leu Gln Trp Ala Lys Lys Gly Tyr Tyr Gly Met Lys Ser Asn
1               5                   10                  15
```

<210> SEQ ID NO 21
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 21

```
Val Leu Gln Trp Ala Lys Lys Gly Tyr Tyr Thr Gly Lys Ser Asn
1               5                   10                  15
```

<210> SEQ ID NO 22
<211> LENGTH: 17
<212> TYPE: PRT
<213> ORGANISM: Artificial Sequence
<220> FEATURE:
<223> OTHER INFORMATION: Synthetic Peptide

<400> SEQUENCE: 22

```
Ile Ser Gln Ala Val His Ala Ala His Ala Glu Ile Asn Glu Ala Gly
1               5                   10                  15

Arg
```

```
<210> SEQ ID NO 23
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 23

Tyr Val Gln Gly Lys Ala Asn Leu Lys Ser Lys Leu Met Tyr Thr
1               5                   10                  15

<210> SEQ ID NO 24
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 24

Trp Ala Lys Lys Gly Tyr Tyr Thr Met Lys
1               5                   10

<210> SEQ ID NO 25
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 25

Val Leu Gln Trp Ala Lys Lys Gly Tyr Tyr Thr Met Lys
1               5                   10

<210> SEQ ID NO 26
<211> LENGTH: 24
<212> TYPE: PRT
<213> ORGANISM: Artificial Sequence
<220> FEATURE:
<223> OTHER INFORMATION: Synthetic Peptide

<400> SEQUENCE: 26

Ala Ala Ser Val Leu Gln Trp Ala Lys Lys Gly Tyr Tyr Thr Met Lys
1               5                   10                  15

Ser Asn Leu Val Val Leu Glu Asn
            20

<210> SEQ ID NO 27
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Val Leu Gln Trp Ala Lys Lys Gly Tyr Tyr Thr Met Lys Ser Asn
1               5                   10                  15
```